US011246904B2

(12) United States Patent
Singh

(10) Patent No.: US 11,246,904 B2
(45) Date of Patent: *Feb. 15, 2022

(54) POLYMERIC NANOPARTICLES AND A PROCESS OF PREPARATION THEREOF

(71) Applicant: Hillstream BioPharma Inc., Chester, NJ (US)

(72) Inventor: Harpal Singh, New Delhi (IN)

(73) Assignee: Hillstream BioPharma, Inc., Chester, NJ (US)

(*) Notice: Subject to any disclaimer, the term of this patent is extended or adjusted under 35 U.S.C. 154(b) by 161 days.

This patent is subject to a terminal disclaimer.

(21) Appl. No.: 16/117,303

(22) Filed: Aug. 30, 2018

(65) Prior Publication Data

US 2019/0091280 A1    Mar. 28, 2019

Related U.S. Application Data

(63) Continuation of application No. 14/396,594, filed as application No. PCT/IB2013/001247 on Apr. 22, 2013, now Pat. No. 10,092,617.

(60) Provisional application No. 61/714,994, filed on Oct. 17, 2012.

(30) Foreign Application Priority Data

Apr. 23, 2012   (IN) .................. IN1249/DEL/2012

(51) Int. Cl.
*A61K 38/08*     (2019.01)
*A61K 9/00*      (2006.01)
*A61K 9/51*      (2006.01)
*A61K 47/34*     (2017.01)
*B82Y 30/00*     (2011.01)
*A61K 31/337*    (2006.01)
*A61K 31/454*    (2006.01)
*A61K 31/473*    (2006.01)
*A61K 31/505*    (2006.01)
*C08G 63/664*    (2006.01)
*A61K 47/69*     (2017.01)
*A61K 31/704*    (2006.01)

(52) U.S. Cl.
CPC ............ *A61K 38/08* (2013.01); *A61K 9/0019* (2013.01); *A61K 9/5146* (2013.01); *A61K 9/5153* (2013.01); *A61K 31/337* (2013.01); *A61K 31/454* (2013.01); *A61K 31/473* (2013.01); *A61K 31/505* (2013.01); *A61K 31/704* (2013.01); *A61K 47/34* (2013.01); *A61K 47/6933* (2017.08); *A61K 47/6935* (2017.08); *A61K 47/6937* (2017.08); *B82Y 30/00* (2013.01); *C08G 63/664* (2013.01); *Y10T 428/2982* (2015.01)

(58) Field of Classification Search
CPC ............... A61K 38/08; A61K 47/6933; A61K 47/6935; A61K 47/6937; A61K 31/337; A61K 31/454; A61K 31/473; A61K 31/505; A61K 9/5146; A61K 31/704; A61K 9/0019; A61K 9/5153; A61K 47/34; C08G 63/664; B82Y 30/00; Y10T 428/2982; A61P 3/10; A61P 35/00
See application file for complete search history.

(56) References Cited

U.S. PATENT DOCUMENTS

| | | |
|---|---|---|
| 6,322,805 B1 | 11/2001 | Kim et al. |
| 9,551,111 B2 | 1/2017 | Restorp et al. |
| 2006/0165987 A1 | 7/2006 | Hildgen et al. |
| 2008/0081075 A1 | 4/2008 | Hsiue et al. |
| 2008/0268063 A1 | 10/2008 | Jon et al. |
| 2010/0004398 A1 | 1/2010 | Wang et al. |
| 2010/0129456 A1 | 5/2010 | Ishihara et al. |
| 2011/0003007 A1 | 1/2011 | Kakizawa et al. |
| 2011/0251246 A1 | 10/2011 | Kufe |

FOREIGN PATENT DOCUMENTS

| | | |
|---|---|---|
| CN | 102000340 A | 4/2011 |
| CN | 102276813 A | 12/2011 |
| JP | H10512287 A | 11/1998 |
| JP | 2009185261 A | 8/2009 |
| JP | 2015507621 A | 3/2015 |
| WO | 2003/086369 A2 | 10/2003 |
| WO | 2006/014626 A2 | 2/2006 |
| WO | 2008/139804 A1 | 11/2008 |
| WO | 2009/104706 A1 | 8/2009 |

(Continued)

OTHER PUBLICATIONS

Onishi (Biol. Pharm. Bull. 26(1) 116-119 (2003)).*
Mosquiera (Journal of Drug Targeting. 1999. vol. 1. No. I, pp. 65-78).*
Essa (European Journal of Pharmaceutics and Biopharmaceutics 75 (2010) 96-106).*
Wang (Int J Nanomedicine. 2011;6:1443-51. doi: 10.2147/IJN. S19765. Epub Jul. 7, 2011).*
Kim (Journal of Controlled Release vol. 157, Issue 2, Jan. 30, 2012, pp. 279-286).*

(Continued)

*Primary Examiner* — Matthew P Coughlin
*Assistant Examiner* — Thurman Wheeler
(74) *Attorney, Agent, or Firm* — Dechert LLP

(57) ABSTRACT

The present invention relates to the field of nanotechnology, in particular, to the production of biodegradable polymeric nanoparticles. The present invention provides a biodegradable polymeric nanoparticle made up of a block copolymer and a process for producing the same. The nanoparticles are produced without the use of any emulsifiers and have a size ranging from 30-120 nm. The methods of controlling the drug loading capacity are disclosed along with the process of producing entity-loaded nanoparticles. Compositions comprising the nanoparticles and their use in therapeutics, diagnostics and theranostics are also disclosed.

18 Claims, 15 Drawing Sheets

Specification includes a Sequence Listing.

(56) References Cited

FOREIGN PATENT DOCUMENTS

WO     2012/024530 A2     2/2012

OTHER PUBLICATIONS

Farokhzad (Cancer Research 64, 7668-7672, Nov. 1, 2004).*
HiMedia (http://himedialabs.com/TD/TC222.pdf, accessed Aug. 30, 2020).*
Borchard et al., "The Role of Serum Complement on the Organ Distribution of Intravenously Administered Poly (methylmethacrylate) Nanoparticles: Effects of Pre-Coating with Plasma and with Serum Complement." Pharmaceutical Research. 1996, 13(7):1055-1058.
Cho, et al., "Therapeutic Nanoparticles for Drug Delivery in Cancer." Clin. Cancer Res. 2008, 14:1310-1316.
Farokhzad, OC, et al., "Targeted nanoparticle-aptamer bioconjugates for cancer chemotherapy in vivo." Proc. Natl. Avad. Sci. USA. 2006, 103(16):6315-20.
Fonseca et al., "Paclitaxel-loaded PLGA nanoparticles: preparation, physicochemical characterization and in vitro anti-tumoral activity." J. Controlled Release. 2002, 83(2):273-86.
Hood et al., "Nanocarriers for vascular delivery of antioxidants." Nanomedicine (Lond). 2011, 6(7):1257-1272.
Jain et al., "PEG-PLA-PEG block copolymeric nanoparticles for oral immunization against hepatitis B." International Journal of Pharmaceuticals. 2010, 387:253-262.
Essa et al., "Characterization of rhodamine loaded PEG-g-PLA nanoparticles (NPs): Effect of poly(ethylene glycol) grafting density." International Journal of Pharmaceuticals. 2011, 411:178-187.
International Search Report from PCT/IB2013/001247 dated Jan. 21, 2014.
International Preliminary Report on Patentability from PCT/IB2013/001247 dated Oct. 28, 2014.
Kim, S.Y. et al., 'Poly(ethylene oxide)-poly(propylene oxide)-poly(ethylene oxide) /poly(e-caprolactone) (PCL) amphiphilic block copolymeric nanospheres II. Thermo-responsive drug release behaviors.' Journal of Controlled Release. 2000, 65:345-358.
Sosnik et al., "Polymeric Nanocarriers: New Endeavors for the Optimization of the Technological Aspects of Drugs." Recent Patents on Biomedical Engineering. 2008, 1:43-59.
Spada et al., "Protein delivery of polymeric nanoparticles." World Academy of Science, Engineering and Technology. 2011, 76.
Sundar et al., "Biopolymeric nanoparticles." Science and Technology of Advanced Materials. 2010, 11:1-13.
Notice of Reasons for Rejection corresponding to Japanese Patent Application No. 2015-507621, dated Jun. 15, 2017.
Kim et al. (1998) "Preparation and characterization of biodegradable nanospheres composed of methoxy poly(ethylene glycol) and DL-lactide block copolymer as novel drug carriers," J. Control. Release. 56:197-208.
Yoo Hyuk Sang et al. (2001) "Biodegradable polymeric micelles composed of doxorubicin conjugated PLGA-PEG block copolymer," Journal of Controlled Release. 70:63-70.
Yoo Hyuk Sang et al. (1999) "Biodegradable nanoparticles containing doxorubicin-PLGA conjugate for sustained release," Pharmaceutical Research. 16(7):1114-8.
Xiong et al. (2003) "Synthesis and Aggregation Behavior of Pluronic F127/Poly(lactic acid) Block Copolymers in Aqueous Solutions," Macromolecules. 36(26):9979-9985.
Perego et al. (1996) "Effect of molecular weight and crystallinity on poly(lactic acid) mechanical properties," Journal of Applied Polymer Science 59(1):37-43.
Kunii et al. (2007) "Preparation and antitumor characteristics of PLA/(PEG-PPG-PEG) nanoparticles loaded with camptothecin," Eur J Pharm Biopharm. 67(1):9-17.
Japanese Patent Office, Official Action issued in corresponding JP Application No. 2020-179393, dated Nov. 12, 2021, 12 pages, with English Translation.

* cited by examiner

POLYMERIC NANOPARTICLES AND A PROCESS OF PREPARATION THEREOF

CROSS REFERENCE TO RELATED APPLICATIONS

This application is a continuation of U.S. patent application Ser. No. 14/396,594, filed on Oct. 23, 2014, which is a 371 of PCT/US13/01247, filed Apr. 22, 2013, which is a national stage entry of Indian Patent Application 1249/DEL/ 2012, filed Apr. 23, 2012, as well as U.S. Provisional Application No. 61/714,994, filed Oct. 17, 2012. The contents of each of these applications are incorporated herein by reference in their entireties.

FIELD OF INVENTION

The present invention relates to the field of nanotechnology, in particular, to the production of biodegradable polymeric nanoparticles. The present invention also relates to a method of producing biodegradable polymeric nanoparticles capable of carrying therapeutic agents and/or targeting agents. These biodegradable polymeric nanoparticles have immense potential in therapeutics, diagnostics and theranostics.

BACKGROUND OF THE INVENTION

Molecularly targeted therapy has emerged as a promising approach to overcome the lack of specificity of conventional chemotherapeutic agents in the treatment of cancer. Synthetic peptide drugs in cancer therapy show high specificity, stability and ease of synthesis compared to conventional proteins. However, the delivery of these anti-cancer peptides to the target site poses huge problems due to factors like enzymatic degradation, immunogenicity and a short life span in the blood. Targeted delivery of anticancer drugs would be more effective if the delivery system was able to reach the desired tumor tissues through the penetration of barriers in the body with minimal loss of their volume or activity in the blood circulation and selectively kill tumor cells. This would improve patient survival and quality of life by increasing the intracellular concentration of drugs and reducing dose-limiting toxicities simultaneously. One of the strategies for delivery of peptide drugs involves conjugating peptides with cell penetrating peptides (CPP) for direct delivery of the drug into cytosol. However, conjugation with CPP increases the cost and decreases the efficacy and stability of peptide drugs, and can in some instances increase toxicity. Some peptidic therapeutic agents like NuBCP-9 and Bax-BH3 show selective binding to cancerous cells and initiate apoptosis. Unfortunately, free drug formulations of peptidic therapeutic agents require the use of large amounts and frequent administration of the peptide, thereby increasing the cost and inconvenience of therapy.

There is a pressing need for a delivery system that can effectively deliver therapeutic agents, including therapeutic peptides, into the cytosol of cancerous cells.

SUMMARY

Provided herein is a biodegradable block copolymer, a nanoparticle formed of the biodegradable block copolymer, processes for the preparation thereof, compositions thereof, uses thereof as a carrier for various entities including therapeutic and targeting agents, and methods for the treatment of disease. These polymeric nanoparticles are non-toxic and biodegradable, have a tunable size, and can increase the half life of the encapsulated drug in vivo.

One aspect of the present invention is a biodegradable polymeric nanoparticle formed of a block copolymer consisting essentially of poly(lactic acid) (PLA) chemically modified with a hydrophilic-hydrophobic block copolymer, wherein said hydrophilic-hydrophobic block copolymer is selected from a block copolymer consisting essentially of poly(methyl methacrylate)-poly(methylacrylic acid) (PMMA-PMAA), poly(styrene-polyacrylic) acid (PS-PAA), poly(acrylic acid)-poly(vinylpyridine) (PAA-PVP), poly (acrylic acid)-poly(N,N-dimethylaminoethyl methacrylate) (PAA-PDMAEMA), poly(ethylene glycol)-poly(butylene glycol) (PEG-PBG), and poly(ethylene glycol)-poly(propylene glycol)-poly(ethylene glycol) (PEG-PPG-PEG).

In one embodiment, the biodegradable polymeric nanoparticle is formed of the block copolymer PLA-PEG-PPG-PEG.

In some embodiments, the poly(lactic acid) (PLA) component of the biodegradable polymeric nanoparticle has an average molecular weight of about 4,000 g/mol to 90,000 g/mol. In some embodiments, the poly(ethylene glycol)-poly(propylene glycol)-poly(ethylene glycol) (PEG-PPG-PEG) component of the biodegradable polymeric nanoparticle has an average molecular weight in the range of about 4,000 g/mol to 15,000 g/mol.

In another embodiment, the biodegradable nanoparticle is formed of the block copolymer PLA-PEG-PPG-PEG-PLA.

In some embodiments, the PLA is chemically modified with a hydrophilic-hydrophobic block copolymer using a covalent bond.

In some embodiments, the size of the biodegradable polymeric nanoparticle is in the range of 30-120 nm.

In some embodiments, the biodegradable polymeric nanoparticle is either substantially free of emulsifier, or further comprises external emulsifier of about 0.5% to 5% by weight.

In an embodiment, the average molecular weight of the poly(lactic acid) block is in the range of about 4,000 g/mol to 90,000 g/mol, the average molecular weight of the PEG-PPG-PEG block is in the range of about 4,000 g/mol to 15,000 g/mol, and the external emulsifier is about 0.5% to 5% by weight.

In another embodiment, the average molecular weight of the poly(lactic acid) block is less than or equal to about 16,000 g/mol, the average molecular weight of the PEG-PPG-PEG block is in the range of about 4,000 g/mol to 15,000 g/mol, and the composition is substantially free of emulsifier.

In some embodiments, the biodegradable polymeric nanoparticle further comprises a therapeutic agent. The therapeutic agent can be encapsulated, surface conjugated, or adsorbed on the biodegradable polymeric nanoparticle. The therapeutic agent can be selected from a group comprising small organic molecules, nucleic acids, polynucleotides, oligonucleotides, nucleosides, DNA, RNA, amino acids, peptides, proteins, antibiotics, low molecular weight molecules, chemotherapeutics, drugs, metal ions, dyes, radioisotopes, contrast agents and imaging agents.

In a further embodiment, the therapeutic agent is an anti-cancer peptide. In an embodiment, the anti-cancer peptide is either FSRSLHSLL (SEQ ID NO:1) or any polypeptide substantially incorporating the FSRSLHSLL (SEQ ID NO:1), wherein the FSRSLHSLL (SEQ ID NO:1) is in either the D or L-configuration. In another embodiment, the anti-cancer peptide is chemically modified with a hydrophobic polymer. In one embodiment, the anticancer peptide is FSRSLHSLL (SEQ ID NO:1) chemically modified with poly(lactic acid).

In other embodiments, the anti-cancer peptide comprises a sequence or a modified sequence from the MUC1-CD domain such as either CQCRRKN (SEQ ID NO:2) or AQARRKN (SEQ ID NO:4).

In other embodiments, the anti-cancer peptide comprising a sequence or a modified sequence from the MUC1-CD can be linked to a protein transduction domain such as polyarginine. In some embodiments, polyarginine is composed of nine arginine residues.

In further embodiments, the therapeutic agents are chemotherapeutics including, but not limited to, paclitaxel, doxorubicin, pimozide, perimethamine, indenoisoquinolines, or nor-indenoisoquinolines.

In another embodiment, the therapeutic agent is insulin.

In some embodiments, the biodegradable polymeric nanoparticle further comprises a targeting moiety selected from the group consisting of vitamins, small molecule drugs, ligands, amines, peptide fragments, antibodies, and aptamers. In a specific embodiment, the targeting moiety is folic acid.

Another aspect of this invention provides for a process for preparing biodegradable polymeric nanoparticles comprising:

a. dissolving poly-lactic acid (PLA) and a hydrophilic-hydrophobic block copolymer in an organic solvent to obtain a solution;

b. adding a carbodiimide coupling agent and a base to the solution to obtain a reaction mixture;

c. stirring the reaction mixture to obtain a block copolymer of PLA chemically modified with the hydrophilic-hydrophobic block copolymer;

d. dissolving the block copolymer from step (c) in an organic solvent and homogenizing to obtain a homogenized mixture;

e. adding the homogenized mixture to an aqueous phase to obtain an emulsion; and f. stirring the emulsion to obtain biodegradable polymeric nanoparticles.

In an embodiment, the process optionally comprises the steps of washing the biodegradable polymeric nanoparticles with water and drying the biodegradable polymeric nanoparticles.

In a further embodiment, the process results in biodegradable polymeric nanoparticles having a size in the range of 30-120 nm.

In another embodiment, the process optionally comprises adding emulsifier in step (a).

A further aspect of the present invention provides a process for preparing biodegradable polymeric nanoparticles further comprising a therapeutic agent, wherein the process comprises:

a. homogenizing a therapeutic agent with the biodegradable polymeric nanoparticles described above in an organic solvent to obtain a primary emulsion;

b. further emulsifying the primary emulsion of step (a) in an aqueous phase to obtain a secondary emulsion; and c. stirring the secondary emulsion to obtain the polymeric nanoparticles further comprising a therapeutic agent.

In an embodiment, the process optionally comprises the steps of washing the biodegradable polymeric nanoparticles comprising the therapeutic agent with water and drying the biodegradable polymeric nanoparticles.

In some embodiments, the process comprises incorporation of a therapeutic agent selected from a group consisting of small organic molecules, nucleic acids, polynucleotides, oligonucleotides, nucleosides, DNA, RNA, amino acids, peptides, protein, antibiotics, low molecular weight molecules, chemotherapeutics, drugs, metal ions, dyes, radioisotopes, contrast agents and imaging agents. In a further embodiment, the therapeutic agent is an anticancer peptide, wherein the anticancer peptide is either FSRSLHSLL (SEQ ID NO:1), or any polypeptide substantially incorporating the FSRSLHSLL (SEQ ID NO:1), and wherein the FSRSLHSLL (SEQ ID NO:1) is in either the D or L-configuration. In a specific embodiment, the anticancer peptide is chemically modified with a hydrophobic polymer. One embodiment is the anticancer peptide FSRSLHSLL (SEQ ID NO:1) chemically modified with poly(lactic acid).

In other embodiments, the anti-cancer peptide is a sequence or a modified sequence from the MUC1-CD domain such as either CQCRRKN (SEQ ID NO:2) or AQARRKN (SEQ ID NO:4).

In other embodiments, the anti-cancer peptide comprising a sequence or a modified sequence from the MUC1-CD can be linked to a protein transduction domain such as polyarginine. In some embodiments, polyarginine is composed of nine arginine residues.

In further embodiments, the therapeutic agents are chemotherapeutics including, but not limited to, paclitaxel, doxorubicin, pimozide, perimethamine, indenoisoquinolines, or nor-indenoisoquinolines.

A further aspect of the present invention is a process for preparing biodegradable polymeric nanoparticles comprising a PLA-PEG-PPG-PEG tetra block copolymer, wherein the biodegradable polymeric nanoparticles further comprise a free or modified therapeutic agent, wherein the process comprises:

a. homogenizing the therapeutic agent with the biodegradable polymeric nanoparticles of PLA-PEG-PPG-PEG tetra block copolymer in an organic solvent to obtain a primary emulsion;

b. further emulsifying the primary emulsion of step (a) in an aqueous phase to obtain a secondary emulsion; and c. stirring the secondary emulsion to obtain the biodegradable polymeric nanoparticles of PLA-PEG-PPG-PEG comprising the free or modified therapeutic agent.

In an embodiment, the molecular weight of PLA is in the range of about 3,000 g/mol to 10,000 g/mol. In another embodiment, the molecular weight of PLA is in the range of about 4,000 g/mol to 90,000 g/mol.

In some embodiments, the molecular weight of the PEG-PPG-PEG hydrophilic-hydrophobic block copolymer is in the range of about 4,000 g/mol to 15,000 g/mol.

In a further embodiment, the therapeutic agent is covalently attached to a hydrophobic polymer. In an embodiment, the therapeutic agent is covalently attached to poly(lactic acid).

Another aspect of the invention provided herein is the biodegradable polymeric nanoparticles of PLA-PEG-PPG-PEG block copolymer obtained by the processes of the instant application.

Another aspect is a method for treating disease comprising administering biodegradable polymeric nanoparticles of PLA-PEG-PPG-PEG further comprising at least one therapeutic agent, to a subject in need thereof.

In some embodiments, the disease is cancer, and the therapeutic agent is either an anti-cancer peptide or a chemotherapeutic. In some embodiments, the cancer is breast cancer, and the anti-cancer peptide is a sequence or modified sequence from the MUC1-CD domain such as CQCRRKN (SEQ ID NO:2) or AQARRKN (SEQ ID NO:4).

In other embodiments, the anti-cancer peptide comprising a sequence or a modified sequence from the MUC1-CD can be linked to a protein transduction domain such as polyarginine. In some embodiments, polyarginine is composed of nine arginine residues.

In a particular embodiment, the disease is diabetes, and the therapeutic agent is insulin.

An additional aspect of the present invention is a pharmaceutical composition comprising a biodegradable polymeric nanoparticle of the instant invention, and at least one pharmaceutically acceptable carrier.

In one embodiment, the pharmaceutical composition is suitable for delivery in a subject by either intravenous injection, intramuscular injection, or oral routes.

A further aspect is a block copolymer consisting essentially of a segment of poly(lactic acid) (PLA) and a segment of poly(ethylene glycol)-poly(propylene glycol)-poly(ethylene glycol) (PEG-PPG-PEG).

Another aspect is a conjugate comprising a therapeutic agent covalently attached to a hydrophobic polymer. In some embodiments, the therapeutic agent is covalently attached to poly(lactic acid). In some embodiments, the therapeutic agent is selected from the group consisting of a peptide, protein and polypeptide.

Another aspect provided herein is the process for preparing a conjugate comprising a therapeutic agent covalently attached to poly(lactic acid), wherein the process comprises reaction of the therapeutic agent and poly(lactic) acid in the presence of a carbodiimide coupling agent and a hydroxyderivative.

A further aspect of is a method for treating disease comprising administering biodegradable polymeric nanoparticles of PLA-PEG-PPG-PEG further comprising at least one therapeutic agent covalently attached to poly(lactic acid), to a subject in need thereof.

BRIEF DESCRIPTION OF THE FIGURES

The following figures form part of the present specification and are included to further illustrate aspects of the present invention. The invention may be better understood by reference to the figures in combination with the detailed description of the specific embodiments presented herein.

DETAILED DESCRIPTION OF THE INVENTION

Figure 1:
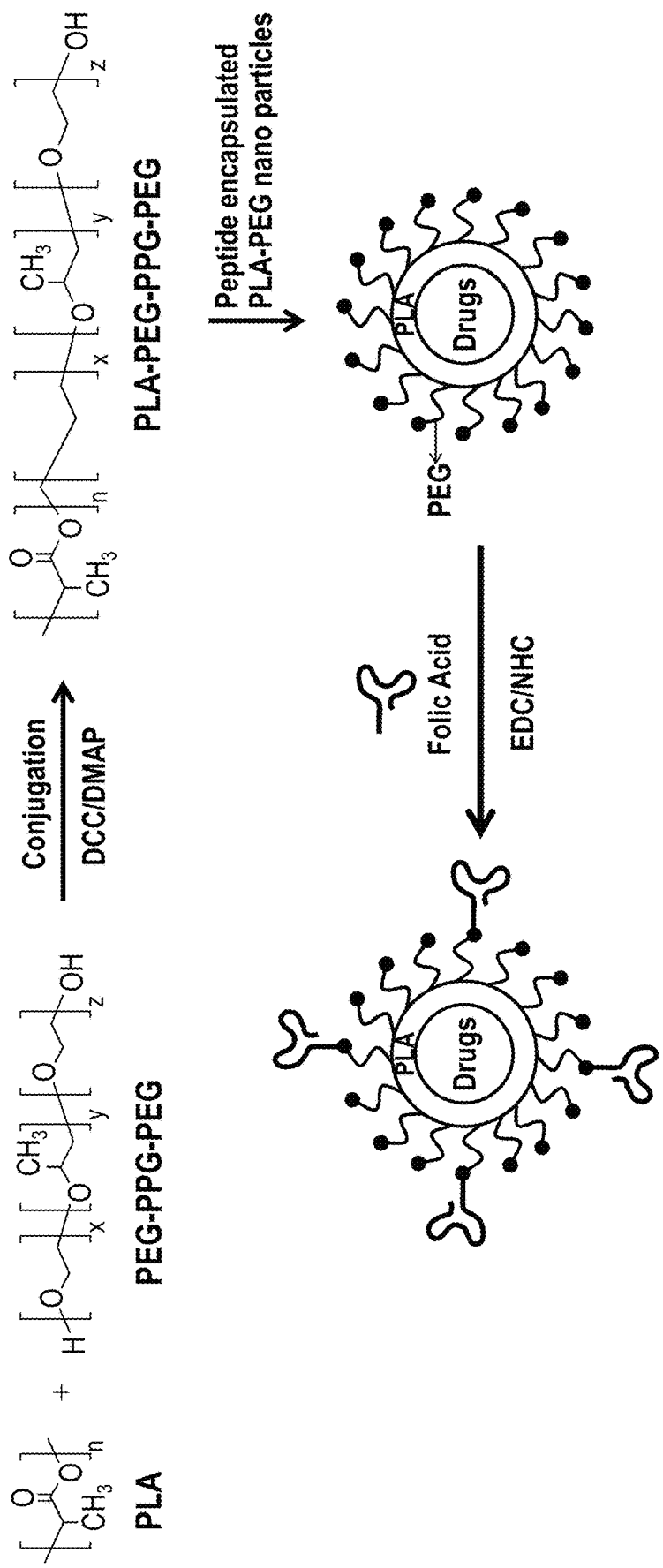
FIG. 1 provides the schematic diagram of the polymeric nanoparticles of PLA-PEG-PPG-PEG block copolymer.

Nanoparticles can be produced as nanocapsules or nanospheres. Protein loading in the nanoparticle can be carried out by either the adsorption process or the encapsulation process (Spada et al., 2011; Protein delivery of polymeric nanoparticles; *World Academy of Science, Engineering and Technology:* 76). Nanoparticles, by using both passive and active targeting strategies, can enhance the intracellular concentration of drugs in cancer cells while avoiding toxicity in normal cells. When nanoparticles bind to specific receptors and enter the cell, they are usually enveloped by endosomes via receptor-mediated endocytosis, thereby bypassing the recognition of P-glycoprotein, one of the main drug resistance mechanisms (Cho et al., 2008, Therapeutic Nanoparticles for Drug Delivery in Cancer, *Clin. Cancer Res.,* 2008, 14:1310-1316). Nanoparticles are removed from the body by opsonization and phagocytosis (Sosnik et al., 2008; Polymeric Nanocarriers: New Endeavors for the Optimization of the Technological Aspects of Drugs; Recent Patents on Biomedical Engineering, 1: 43-59). Nanocarrier based systems can be used for effective drug delivery with the advantages of improved intracellular penetration, localized delivery, protect drugs against premature degradation, controlled pharmacokinetic and drug tissue distribution profile, lower dose requirement and cost effectiveness (Farokhzad O C, Cheng J, Teply B A, Sherifi I, Jon S, Kantoff P W; Targeted nanoparticle-aptamer bioconjugates for cancer chemotherapy in vivo. *Proc. Natl. Acad. Sci. USA* 2006, 103 (16): 6315-20; Fonseca C, Simoes S, Gaspar R E, Paclitaxel-loaded PLGA nanoparticles: preparation, physicochemical characterization and in vitro anti-tumoral activity. *J. Controlled Release* 2002; 83 (2): 273-86; Hood et al., *Nanomedicine,* 2011, 6(7):1257-1272).

The uptake of nanoparticles is indirectly proportional to their small dimensions. Due to their small size, the polymeric nanoparticles have been found to evade recognition and uptake by the reticulo-endothelial system (RES), and can thus circulate in the blood for an extended period (Borchard et al., 1996, *Pharm. Res.* 7: 1055-1058). Nanoparticles are also able to extravasate at the pathological site like the leaky vasculature of a solid tumor, providing a passive targeting mechanism. Due to the higher surface area leading to faster solubilization rates, nano-sized structures usually show higher plasma concentrations and area under the curve (AUC) values. Lower particle size helps in evading the host defense mechanism and increase the blood circulation time. Nanoparticle size affects drug release. Larger particles have slower diffusion of drugs into the system. Smaller particles offer larger surface area but lead to fast drug release. Smaller particles tend to aggregate during storage and transportation of nanoparticle dispersions. Hence, a compromise between a small size and maximum stability of nanoparticles is desired. The size of nanoparticles used in a drug delivery system should be large enough to prevent their rapid leakage into blood capillaries but small enough to escape capture by fixed macrophages that are lodged in the reticuloendothelial system, such as the liver and spleen.

In addition to their size, the surface characteristics of nanoparticles are also an important factor in determining the life span and fate during circulation. Nanoparticles should ideally have a hydrophilic surface to escape macrophage capture. Nanoparticles formed from block copolymers with hydrophilic and hydrophobic domains meet these criteria. Controlled polymer degradation also allows for increased levels of agent delivery to a diseased state. Polymer degradation can also be affected by the particle size. Degradation rates increase with increase in particle size in vitro (Biopolymeric nanoparticles; Sundar et al., 2010, *Science and Technology of Advanced Materials*; doi:10.1088/1468-6996/11/1/014104).

Poly(lactic acid) (PLA) has been approved by the US FDA for applications in tissue engineering, medical materials and drug carriers and poly(lactic acid)-poly(ethylene glycol) PLA-PEG based drug delivery systems are known in the art. US2006/0165987A1 describes a stealthy polymeric biodegradable nano sphere comprising poly(ester)-poly(ethylene) multiblock copolymers and optional components for imparting rigidity to the nanospheres and incorporating pharmaceutical compounds. US2008/0081075A1 discloses a novel mixed micelle structure with a functional inner core and hydrophilic outer shells, self-assembled from a graft macromolecule and one or more block copolymer. US2010/0004398A1 describes a polymeric nanoparticle of shell/core configuration with an interphase region and a process for producing the same.

However, these polymeric nanoparticles essentially require the use of about 1% to 2% emulsifier for the stability of the nanoparticles. Emulsifiers stabilize the dispersed particles in a medium. PVA, PEG, Tween 80 and Tween 20 are some of the common emulsifiers. The use of emulsifiers is however, a cause of concern for in vivo applications as the leaching out of emulsifiers can be toxic to the subject (Safety Assessment on polyethylene glycols (PEGS) and their derivatives as used in cosmetic products, *Toxicology,* 2005 Oct. 15; 214 (1-2): 1-38). The use of emulsifier also increases the mass of the nanoparticle thereby reducing the drug load, leading to higher dosage requirements. Other disadvantages still prevalent in the nanoparticle drug carrier systems are poor oral bioavailability, instability in circulation, inadequate tissue distribution and toxicity. There is a dire need for a delivery system that can effectively deliver therapeutic agents including therapeutic peptides into the cytosol of cancerous cells without the disadvantages presented above.

Provided herein are effective therapeutic delivery systems comprising non-toxic, biodegradable, polymeric nanoparticles with tunable size and which increase the half life of the drug in vivo. Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art. The terms used throughout this specification are defined as follows, unless otherwise limited in specific instances.

The articles "a," "an" and "the" are used to refer to one or to more than one (i.e., to at least one) of the grammatical object of the article.

The terms "comprise" "comprising" "including" "containing" "characterized by" and grammatical equivalents thereof are used in the inclusive, open sense, meaning that additional elements may be included. It is not intended to be construed as "consists of only."

As used herein, "consisting of" and grammatical equivalent thereof exclude any element, step or ingredient not specified in the claim.

As used herein, the term "about" or "approximately" usually means within 20%, more preferably within 10%, and most preferably still within 5% of a given value or range.

The term "biodegradable" as used herein refers to both enzymatic and non-enzymatic breakdown or degradation of the polymeric structure.

As used herein, the term "nanoparticle" refers to particles in the range between 10 nm to 1000 nm in diameter, wherein diameter refers to the diameter of a perfect sphere having the same volume as the particle. The term "nanoparticle" is used interchangeably as "nanoparticle(s)". In some cases, the diameter of the particle is in the range of about 1-1000 nm, 10-500 nm, or 30-120 nm.

In some cases, a population of particles may be present. As used herein, the diameter of the nanoparticles is an average of a distribution in a particular population.

As used herein, the term "polymer" is given its ordinary meaning as used in the art, i.e., a molecular structure comprising one or more repeat units (monomers), connected by covalent bonds. The repeat units may all be identical, or in some cases, there may be more than one type of repeat unit present within the polymer.

The term "nucleic acid" refers to polynucleotides such as deoxyribonucleic acid (DNA), ribonucleic acid (RNA), its variants and derivatives thereof.

As used herein, the term "therapeutic agent" and "drug" are used interchangeably and are also intended to encompass not only compounds or species that are inherently pharmaceutically or biologically active, but materials which include one or more of these active compounds or species, as well as conjugations, modification, and pharmacologically active fragments, and antibody derivatives thereof.

A "targeting moiety" or "targeting agent" is a molecule that will bind selectively to the surface of targeted cells. For example, the targeting moiety may be a ligand that binds to the cell surface receptor found on a particular type of cell or expressed at a higher frequency on target cells than on other cells.

The targeting agent, or therapeutic agent can be a peptide or protein. "Proteins" and "peptides" are well-known terms in the art, and as used herein, these terms are given their ordinary meaning in the art. Generally, peptides are amino acid sequences of less than about 100 amino acids in length, but can include up to 300 amino acids. Proteins are generally considered to be molecules of at least 100 amino acids. The amino acids can be in D- or L-configuration. A protein can be, for example, a protein drug, an antibody, a recombinant antibody, a recombinant protein, an enzyme, or the like. In some cases, one or more of the amino acids of the peptide or protein can be modified, for example by the addition of a chemical entity such as a carbohydrate group, a phosphate group, a farnesyl group, an isofarnesyl group, a fatty acid group, a linker for conjugation, functionalization, or other modification such as cyclization, by-cyclization and any of numerous other modifications intended to confer more advantageous properties on peptides and proteins. In other instances one or more of the amino acids of the peptide or protein can be modified by substitution with one or more non-naturally occurring amino acids. The peptides or proteins may by selected from a combinatorial library such as a phage library, a yeast library, or an in vitro combinatorial library.

As used herein, the term "antibody" refers to any molecule incorporating an amino acid sequence or molecule with secondary or tertiary structural similarity conferring binding affinity to a given antigen that is similar or greater to the binding affinity displayed by an immunoglobulin variable region containing molecule from any species. The term antibody includes, without limitation native antibodies consisting of two heavy chains and two light chains; binding molecules derived from fragments of a light chain, a heavy chain, or both, variable domain fragments, heavy chain or light chain only antibodies, or any engineered combination of these domains, whether monospecific or bispecific, and whether or not conjugated to a second diagnostic or therapeutic moiety such as an imaging agent or a chemotherapeutic molecule. The term includes without limitation immunoglobulin variable region derived binding moieties whether derived from a murine, rat, rabbit, goat, llama, camel, human or any other vertebrate species. The term refers to any such immunoglobulin variable region binding moiety regardless of discovery method (hybridoma-derived, humanized, phage derived, yeast derived, combinatorial display derived, or any similar derivation method known in the art), or production method (bacterial, yeast, mammalian cell culture, or transgenic animal, or any similar method of production known in the art).

The present invention provides a non-toxic, safe, biodegradable polymeric nanoparticle made up of block copolymer and a process for preparing the same. The biodegradable polymeric nanoparticles of the instant invented are formed of a block copolymer consisting essentially of poly(lactic acid) (PLA) chemically modified with a hydrophilic-hydrophobic block copolymer, wherein said hydrophilic-hydrophobic block copolymer is selected from poly(methyl methacrylate)-poly(methylacrylic acid) (PMMA-PMAA), poly(styrene)-poly(acrylic acid) (PS-PAA), poly(acrylic acid)-poly(vinylpyridine) (PAA-PVP), poly(acrylic acid)-poly(N,N-dimethylaminoethyl methacrylate) (PAA-PDMAEMA), poly(ethylene glycol)-poly(butylene glycol) (PEG-PBG), and poly(ethylene glycol)-poly(propylene glycol)-poly(ethylene glycol) (PEG-PPG-PEG).

The present invention provides a process for preparing the biodegradable polymeric nanoparticle of the present invention. The resulting nanoparticle is not only non-toxic, safe, and biodegradable, but is stable in vivo, has high storage stability and can be safely used in a nanocarrier system or drug delivery system in the field of medicine. In fact, the nanoparticles of the instant invention increase the half-life of the deliverable drug or therapeutic agent in-vivo.

The present invention also provides a process for efficient drug loading on a biodegradable polymeric nanoparticle to form an effective and targeted drug delivery nanocarrier system which prevents premature degradation of active agents and has a strong potential for use in cancer therapy.

There is also provided a composition comprising the biodegradable polymeric nanoparticle for use in medicine and in other fields that employ a carrier system or a reservoir or depot of nanoparticles. The nanoparticles of the present invention can be extensively used in prognostic, therapeutic, diagnostic or theranostic compositions. Suitably, the nanoparticles of the present invention are used for drug and agent delivery, as well as for disease diagnosis and medical imaging in human and animals. Thus, the instant invention provides a method for the treatment of disease using the nanoparticles further comprising a therapeutic agent as described herein. The nanoparticles of the present invention can also be use in other applications such as chemical or biological reactions where a reservoir or depot is required, as bio sensors, as agents for immobilized enzymes and the like.

Unexpected and surprising results were obtained when the present inventors attempted to produce biodegradable polymeric nanoparticles without the use of any emulsifiers or stabilizers. The biodegradable polymeric nanoparticles so obtained by the process are safe, stable and non-toxic. In an embodiment, the block copolymer PEG-PPG-PEG is covalently attached to the poly-lactic acid (PLA) matrix, resulting in the block copolymer becoming a part of the matrix, i.e., the nanoparticle delivery system. In contrast, in the prior art, the emulsifier (e.g. PEG-PPG-PEG) is not a part of the nanoparticle matrix and therefore leaches out (FIG. 1). In contrast to nanoparticles of the prior art, there is no leaching out of emulsifier into the medium from the nanoparticles provided herein.

The nanoparticles obtained by the present process are non-toxic and safe due to the absence of added emulsifiers, which can leach out in vivo. The absence or reduced quantity of emulsifier also leads to nanoparticles with a higher drug to polymer ratio. These nanoparticles have higher stability, and an increased storage shelf life as compared to the polymeric nanoparticles present in the art. The polymeric nanoparticles of the present invention are prepared to be biodegradable so that the degradation products may be readily excreted from the body. The degradation also provides a method by which the encapsulated contents in the nanoparticle can be released at a site within the body.

Poly(lactic acid) (PLA), is a hydrophobic polymer, and is the preferred polymer for synthesis of the polymeric nanoparticles of the instant invention. However, poly(glycolic acid) (PGA) and block copolymer of poly lactic acid-co-glycolic acid (PLGA) may also be used. The hydrophobic polymer can also be biologically derived or a biopolymer.

The molecular weight of the PLA used is generally in the range of about 4,000 g/mol to 90,000 g/mol. The average molecular weight of PLA may also be about 60,000 g/mol.

Block copolymers like poly(ethylene glycol)-poly(propylene glycol)-poly(ethylene glycol) (PEG-PPG-PEG), poly(methyl methacrylate)-poly(methylacrylic acid) (PMMA-PMAA), poly(styrene)-poly(acrylic acid) (PS-PAA), poly(acrylic acid)-poly(vinylpyridine) (PAA-PVP), poly(acrylic acid)-poly(N,N-dimethylaminoethyl methacrylate) (PAA-PDMAEMA), poly(ethylene glycol)-poly(butylene glycol) (PEG-PBG) and PG-PR (Polyglycerol (PG) and its copolymers with polyester (PR) including adipic acid, pimelic acid and sebacic acid) are hydrophilic or hydrophilic-hydrophobic copolymers that can be used in the present invention and include ABA type block copolymers such as PEG-PPG-PEG, BAB block copolymers such as PPG-PEG-PPG, $(AB)_n$ type alternating multiblock copolymers and random multiblock copolymers. Block copolymers may have two, three or more numbers of distinct blocks. PEG is a preferred component as it imparts hydrophilicity, anti-phagocytosis against macrophage and resistance to immunological recognition.

In some embodiments, the average molecular weight (Mn) of the hydrophilic-hydrophobic block copolymer is generally in the range of 1,000 to 20,000 g/mol. In a further embodiment, the average molecular weight (Mn) of the hydrophilic-hydrophobic block copolymer is about 4,000 g/mol to 15,000 g/mol. In some cases, the average molecular weight (Mn) of the hydrophilic-hydrophobic block copolymer is 4,400 g/mol, 8,400 g/mol, or 14,600 g/mol.

A block copolymer of the instant invention can consist essentially of a segment of poly(lactic acid) (PLA) and a segment of poly(ethylene glycol)-poly(propylene glycol)-poly(ethylene glycol) (PEG-PPG-PEG).

A specific biodegradable polymeric nanoparticle of the instant invention is formed of the block copolymer poly(lactic acid)-poly(ethylene glycol)-poly(propylene glycol)-poly(ethylene glycol) (PLA-PEG-PPG-PEG).

Another specific biodegradable polymeric nanoparticle of the instant invention is formed of the block copolymer poly(lactic acid)-poly(ethylene glycol)-poly(propylene glycol)-poly(ethylene glycol)-poly(lactic acid) (PLA-PEG-PPG-PEG-PLA).

The biodegradable polymers of the instant invention are formable by chemically modifying PLA with a hydrophilic-hydrophobic block copolymer using a covalent bond.

The biodegradable polymeric nanoparticles of the instant invention have a size in the range of about 30-120 nm.

In an embodiment, the biodegradable polymer of the instant invention is substantially free of emulsifier, or may comprise external emulsifier by an amount of about 0.5% to 5% by weight.

In an embodiment, the biodegradable polymeric nanoparticle of the present invention is PLA-PEG-PPG-PEG, and the average molecular weight of the poly(lactic acid) block is about 60,000 g/mol, the average weight of the PEG-PPG-PEG block is about 8,400 or about 14,600 g/mol, and the external emulsifier is about 0.5% to 5% by weight.

In another embodiment, the biodegradable polymeric nanoparticle of the present invention is PLA-PEG-PPG-PEG, and the an average molecular weight of the poly(lactic acid) block is less than or equal to approximately 16,000 g/mol, the average weight of the PEG-PPG-PEG block is about 8,400 g/mol or about 14,600 g/mol, and wherein the composition is substantially free of emulsifier.

In the present invention, organic solvents useful in the preparation of the nanoparticles prepared herein are suitably acetonitrile ($C_2H_3N$), dimethyl formamide (DMF; $C_3H_7NO$), acetone (($CH_3)_2CO$) and dichloromethane ($CH_2Cl_2$).

The process for preparing biodegradable polymeric nanoparticles of the instant invention comprises dissolving poly(lactic acid) (PLA) and a hydrophilic-hydrophobic block copolymer in an organic solvent to obtain a solution; adding a carbodiimide coupling agent and a base to the solution to obtain a reaction mixture; stirring the reaction mixture to obtain a block copolymer of PLA chemically modified with the hydrophilic-hydrophobic block copolymer; dissolving the block copolymer from the previous step in organic solvent and homogenizing to obtain a homogenized mixture; adding the homogenized mixture to an aqueous phase to obtain an emulsion; and stirring the emulsion to obtain the polymeric nanoparticles.

Carbodiimide coupling agents are well-known in the art. Suitable carbodiimide coupling agents include, but are not limited to, N,N-dicyclohexylcarbodiimide (DCC), N-(3-diethylaminopropyl)-N-ethylcarbodiimide (EDC), and N,N-diisopropylcarbodiimide.

The coupling reaction is usually carried out in the presence of catalysts and/or auxiliary bases such as trialkylamines, pyridine, or 4-dimethylamino pyridine (DMAP).

The coupling reaction can be also carried out in combination with a hydroxyderivative, such as N-hydroxysuccinimide (NHS). Other hydroxyderivatives include, but are not limited to, 1-hydroxybenzotriazole (HOBt), 1-hydroxy-7-azabenzotriazole (HOAt), 6-chloro-1-hydroxybenzotriazole (Cl-HOBt).

The process described above can optionally comprise the additional steps of washing the biodegradable polymeric nanoparticles with water, and drying the polymeric biodegradable polymeric nanoparticles. The process may also optionally comprise a first step of adding emulsifier. The nanoparticles resulting from this process may have a size in the range of 30-120 nm.

In a specific process, the PLA and the copolymer, PEG-PPG-PEG, are dissolved in an organic solvent to obtain a polymeric solution. To this solution, N,N-dicyclohexylcarbodiimide (DCC) is added followed by 4-dimethylaminopyridine (DMAP) at −4° C. to 0° C. The solution is allowed to stir at 250 to 300 rpm at a low temperature ranging from −4° C. to 0° C. for 20 to 28 hours. The nanoparticles of PLA-PEG-PPG-PEG have PLA covalently linked to PEG-PPG-PEG to form a PLA-PEG-PPG-PEG matrix. The nanoparticles are precipitated by an organic solvent like diethyl ether, methanol or ethanol and separated from the solution by conventional methods in the art including filtration, ultracentrifugation or ultrafiltration. The nanoparticles are stored in a temperature ranging from 2° C. to 8° C.

The process of the present invention provides the added advantage of not requiring additional steps of freezing or the use of decoy proteins as none, or a minimal amount, of emulsifiers are used in the process. The present invention is easily carried out in ambient room temperature conditions of 25° C.–30° C. and does not require excessive shearing to obtain the desired small particle size.

Figure 2:
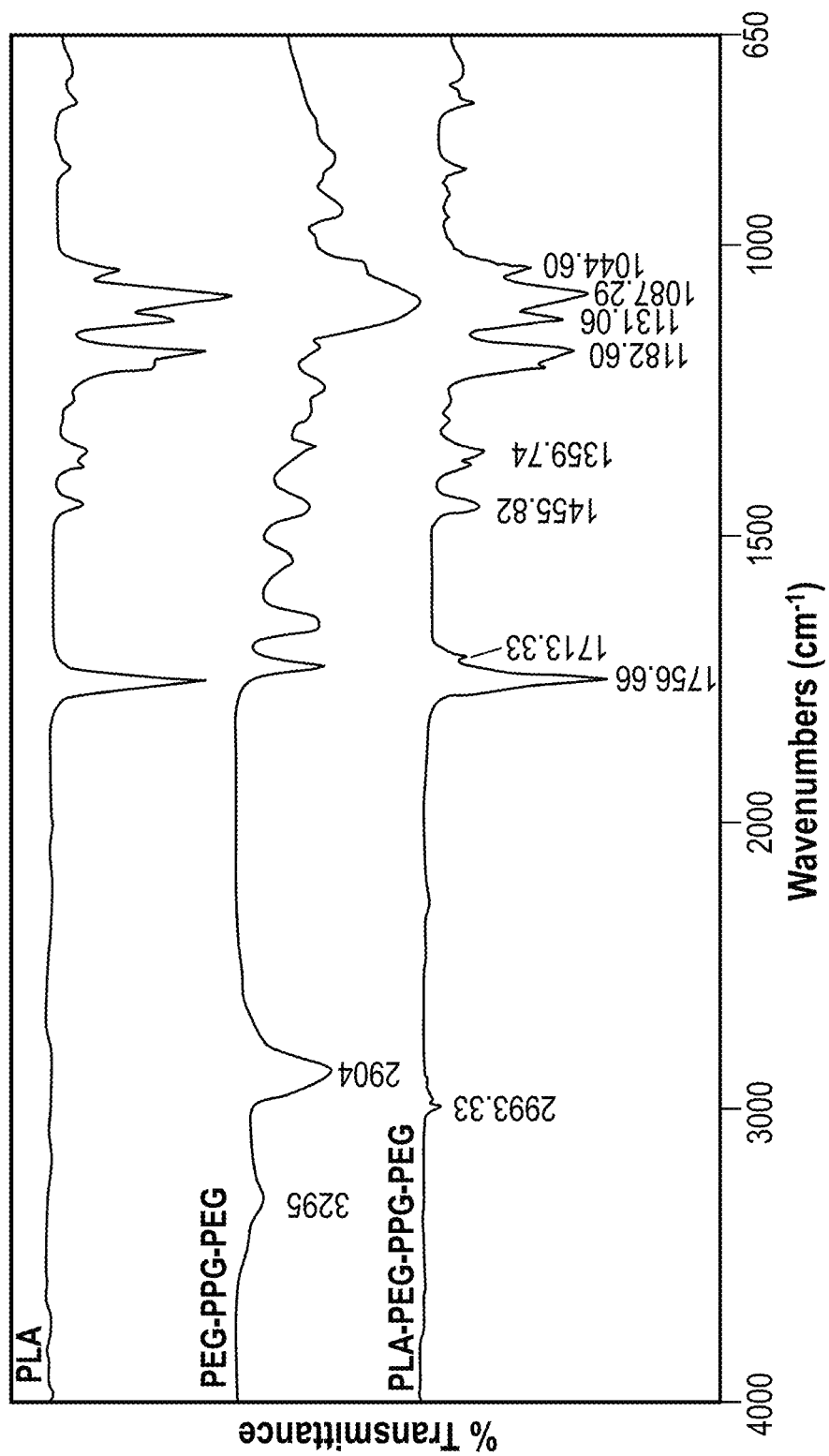
FIG. 2 provides FTIR spectra of PLA, PEG-PPG-PEG and PLA-PEG-PPG-PEG nanoparticles.

A FTIR spectrum of one example of nanoparticles of the present invention is provided in FIG. 2. The NMR spectra of the nanoparticles are provided in FIGS. 3A, 3B, and 3C. The nanoparticle is substantially spherical in configuration as shown in the TEM images of FIGS. 4A and 4B, however, the nanoparticles can adopt a non spherical configuration upon swelling or shrinking. The nanoparticle is amphiphillic in nature. The zeta potential and PDI (Polydispersity Index) of the nanoparticles are provided in Table 2. Storage stability of the nanoparticles of the present invention is better compared to the conventional emulsifier based systems as there is no addition of any free emulsifiers to the process and the block copolymer comprising the PEG moiety is covalently linked in the overall PLA-PEG-PPG-PEG matrix. The storage shelf life of the nanoparticle ranges from 6 to 18 months.

The nanoparticles of the present invention have dimensions ranging from 30-120 nm as measured using a Transmission Electron Microscope (FIG. 4). In suitable embodiments, the diameter of the nanoparticles of the present invention will be less than 200 nm in diameter, and more suitably less than about 100 nm in diameter. In certain such embodiments, the nanoparticles of the present invention will be in the range of about 10 to 200 nm, in the range of about 20 to 150 nm, or in the range of about 30 to 120 nm in diameter.

Figure 5A:
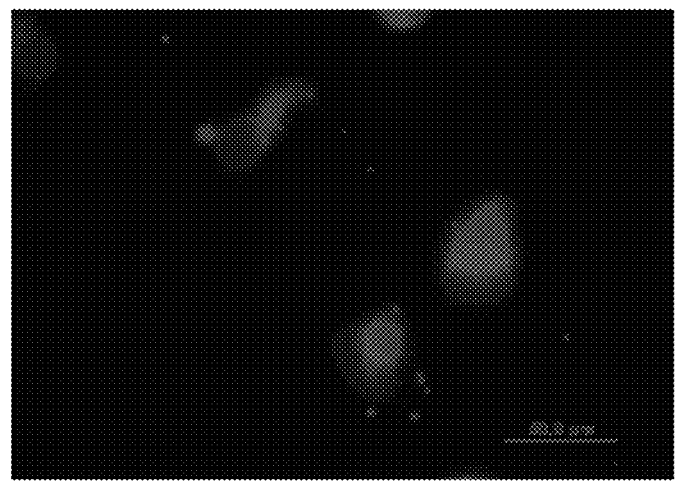
FIGS. 5A, B and C show the cellular internalisation of PLA-PEG-PPG-PEG nanoparticles encapsulating the fluorescent dye, Rhodamine B in MCF-7 cells.
Figure 5B:
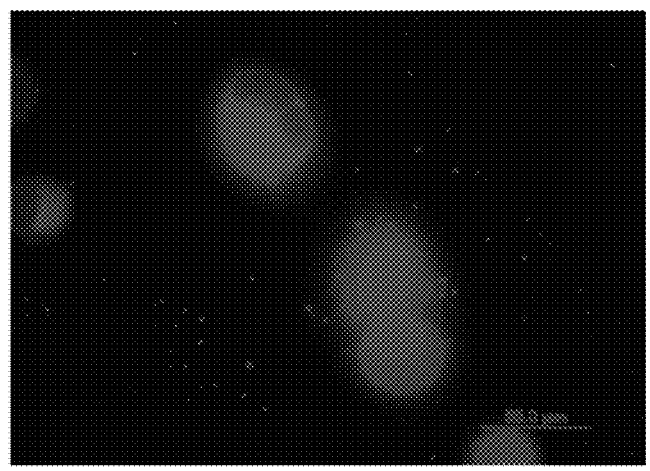
Figure 5C:
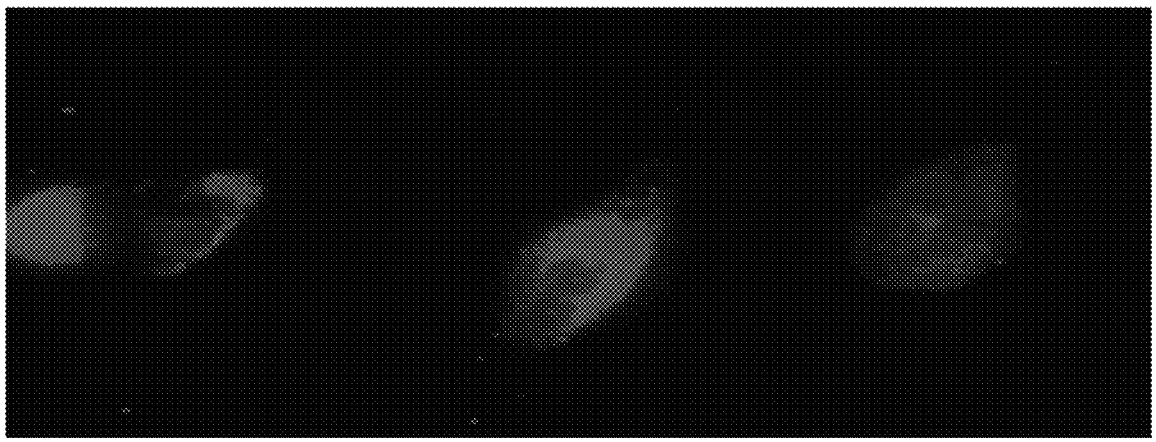
Figure 6A:
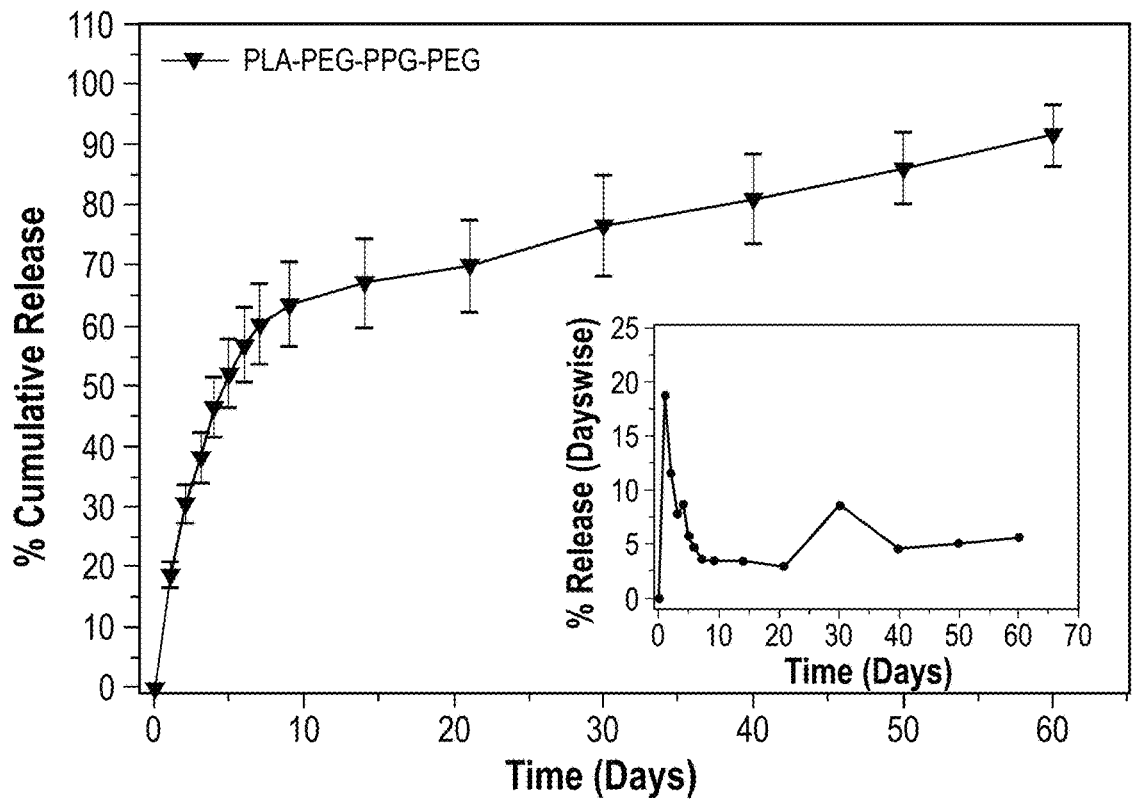
FIG. 6A shows the in-vitro release of encapsulated L-PLBCL2P9 over time from the PLA-PEG-PPG-PEG nanoparticles synthesized using different copolymers at 25° C.

The nanoparticles of the present invention are capable of delivering active agents or entities to specific sites (FIG. 5). The particle size and release properties of the PLA-PEG-PPG-PEG nanoparticle of the present invention can be controlled by varying the molecular weight of the PLA or PEG-PPG-PEG in the polymeric matrix. The release of active agent or entity can be controlled from 12 hrs to 60 days which is an improvement over conventional PLA-PEG systems available in the art (FIG. 6A). The drug loading capacity of the nanoparticle can also be controlled by varying the average molecular weight of the block copolymer in the polymeric matrix of the nanoparticles. There is an increase in the drug loading capacity of the nanoparticle with an increase in the block length of PEG-PPG-PEG block copolymer (Table 3).

As the polymeric nanoparticles made up of PLA-PEG-PPG-PEG block copolymer are amphiphillic in nature, both hydrophobic and hydrophilic drugs can be loaded on the nanoparticles. The nanoparticles of the present invention possess high drug loading capacity due to the absence or minimal use of emulsifiers, resulting in reducing the dose load and frequency of therapeutics. The ratio of active agent or entity to nanoparticle is higher in the nanoparticles of the present invention compared to conventional systems employing emulsifiers, since the weight of the emulsifier can add up to 50% of the total formulation weight (International Journal of Pharmaceutics, 15 Jun. 2011, Volume 411, Issues 1-2, Pages 178-187; International Journal of Pharmaceutics, 2010, 387: 253-262). The nanoparticles help to achieve single and low dose drug delivery coupled with reduced toxicity. The weight percentage of the active agent to the nanocarrier system of PLA-PEG-PPG-PEG ranges from 2-20% to the nanoparticle. The higher drug loading in the nanoparticle reduces the drug dose requirement since the effective dose can be administered at a reduced dosage level. The enhanced internal loading in the polymeric nanoparticles with a prolonged activity of the loaded entities without hampering the total loading capacity of the nanoparticle leads to an effective delivery of highly potential therapeutics. FIG. 7B shows the efficacy of the anticancer peptide, L-NuBCP-9, also referred to herein as "L-PLBCL2P9", (L-configuration of amino acid sequence FSRSLHSLL (SEQ ID NO:1)) loaded into a nanoparticle formulation compared to the free peptide drug formulation and the conventional cell-penetrating peptide conjugated drug formulation in Primary HUVEC cell lines.

Figure 8A:
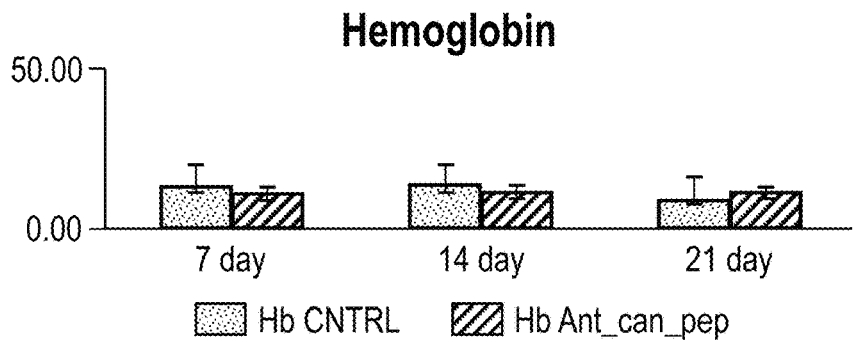
FIG. 8A shows hemoglobin in BALB/c mice treated with plain PLA-PEG-PPG-PEG nanoparticles at a dose of 150 mg/kg body weight.
Figure 8B:
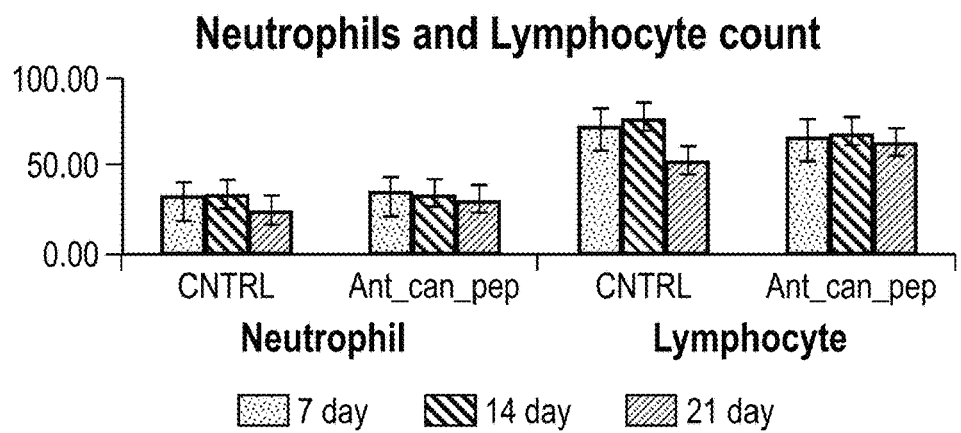
FIG. 8B shows neutrophils and lymphocyte count in BALB/c mice treated with plain PLA-PEG-PPG-PEG nanoparticles at a dose of 150 mg/kg body weight.
Figure 8C:
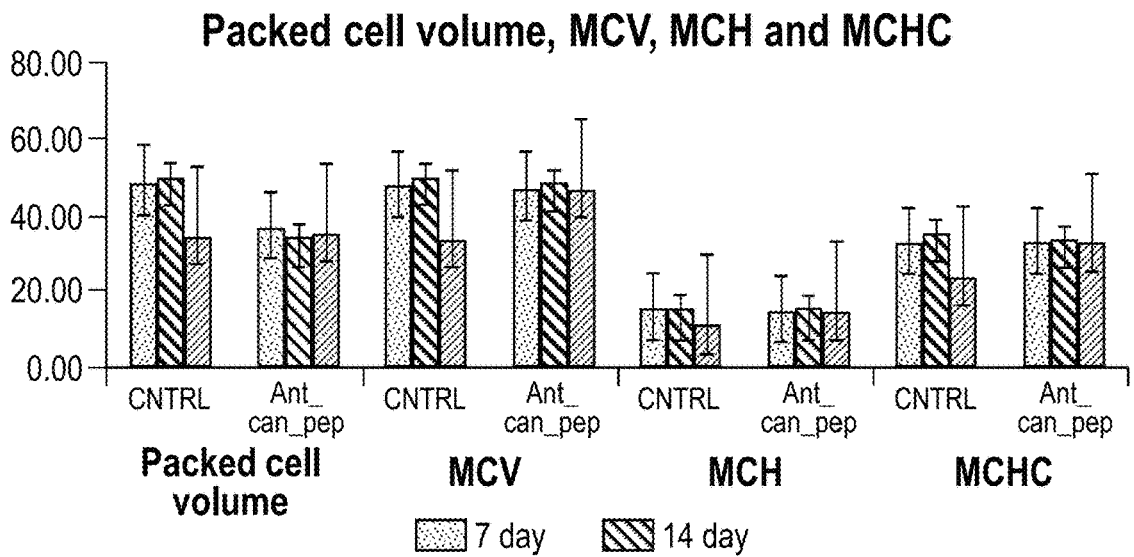
FIG. 8C shows packed cell volume, MCV (Mean Corpuscular Volume), MCH (Mean Corpuscular Hemoglobin) and MCHC (Mean Corpuscular Hemoglobin Concentration), in BALB/c mice treated with plain PLA-PEG-PPG-PEG nanoparticles at a dose of 150 mg/kg body weight.
Figure 9A:
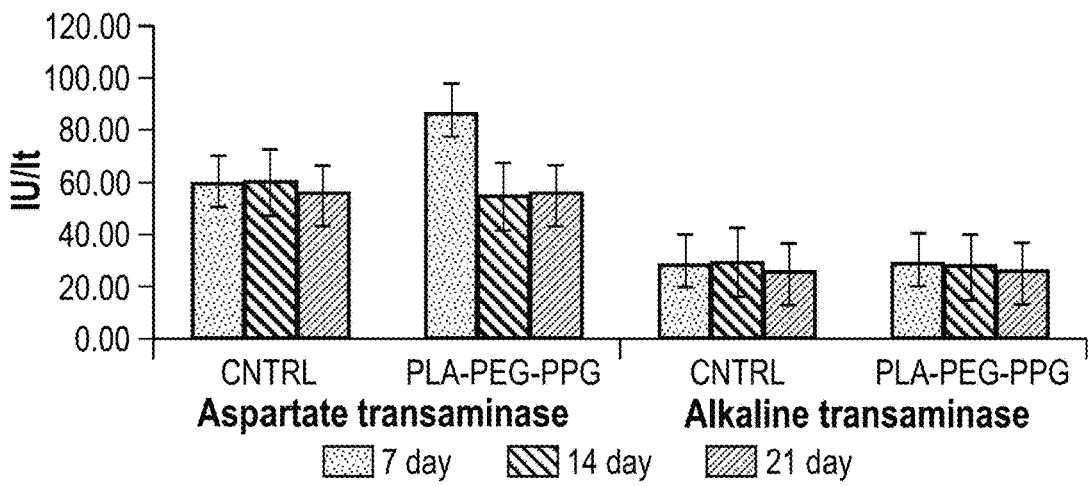
FIG. 9A shows the levels of aspartate transaminase and alanine transaminase in BALB/c mice treated with plain PLA-PEG-PPG-PEG nanoparticles at a dose of 150 mg/kg body weight.
Figure 9B:
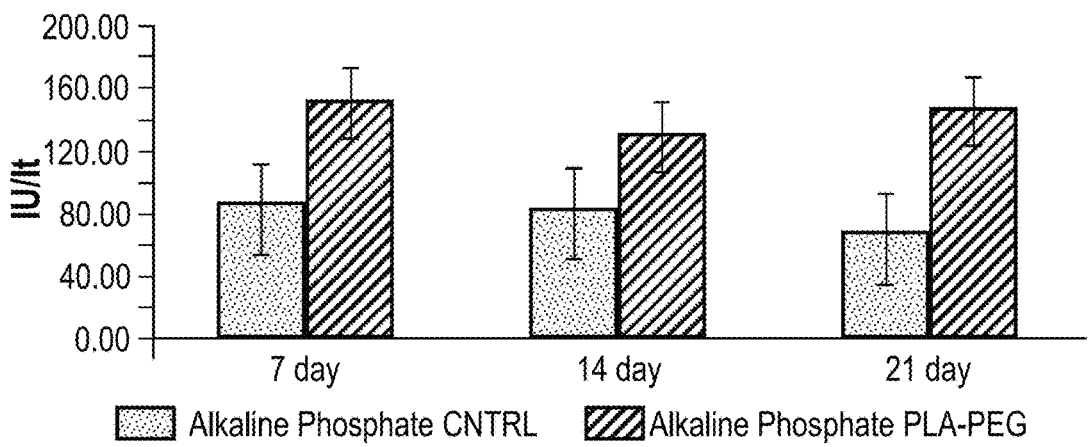
FIG. 9B shows the levels alkaline phosphatase in BALB/c mice treated with plain PLA-PEG-PPG-PEG nanoparticles at a dose of 150 mg/kg body weight.
Figure 9C:
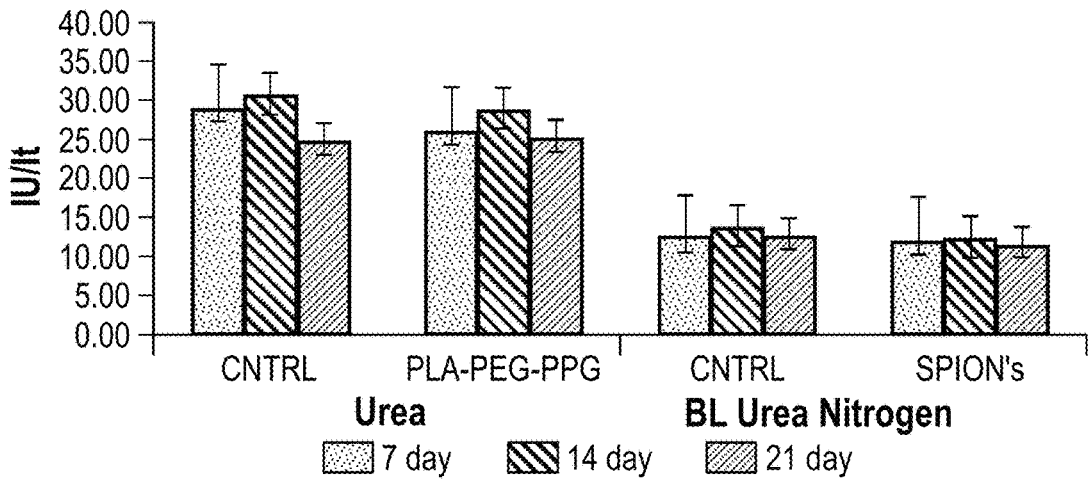
FIG. 9C shows the levels of urea and blood urea nitrogen (BUN) in BALB/c mice treated with plain PLA-PEG-PPG-PEG nanoparticles at a dose of 150 mg/kg body weight.
Figure 10:
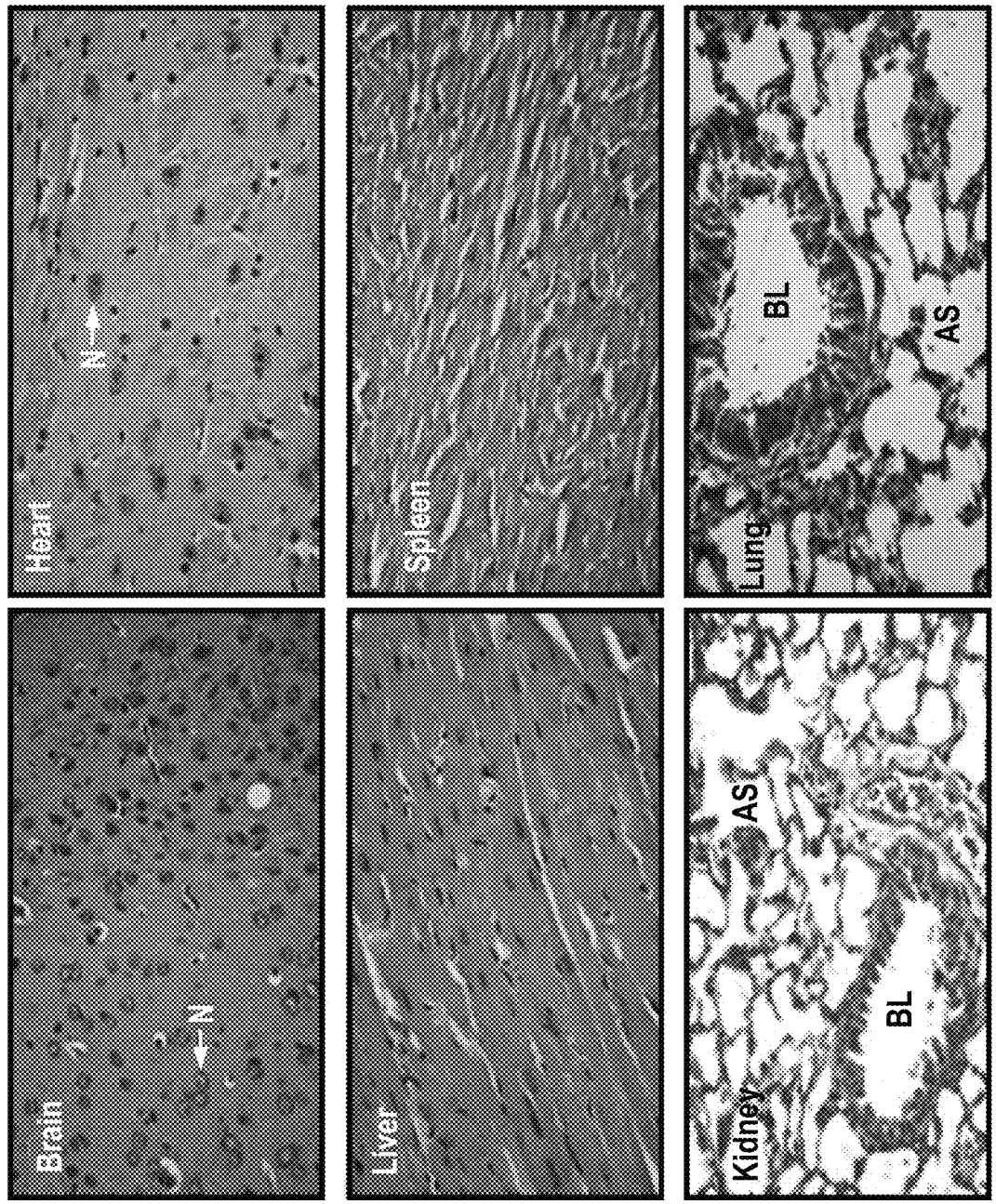
FIG. 10 shows the histopathology of the brain, heart, liver, spleen, kidney and lung of BALB/c mice injected with plain PLA-PEG-PPG-PEG nanoparticles.

The PLA-PEG-PPG-PEG nanoparticles of the present invention are nontoxic as confirmed by in-vitro cell line studies and in-vivo mouse model studies. Hematological parameters assessed in mice treated with PLA-PEG-PPG-PEG nanoparticles at a dose of 150 mg/kg body weight showed no significant change in the complete blood count, red blood count, white blood count, neutrophil and lymphocyte levels with the control group (FIG. 8). Biochemical parameters assessed for liver and kidney functions showed no significant change in the total protein, albumin and globulin levels between the control and the nanoparticle-treated groups. The levels of the liver enzymes, alanine transaminase (ALT), aspartate transaminase (AST) and alkaline phosphatase (ALP) were non-significantly increased in the PLA-PEG-PPG-PEG nanoparticle treated group compared to control group, as seen in FIGS. 9A and 9B. There is no significant change in the levels of urea and blood urea nitrogen (BUN) in mice treated with PLA-PEG-PPG-PEG nanoparticles compared with control (FIG. 9C). The histopathology of the organs, brain, heart, liver, spleen, kidney and lung of mice injected with PLA-PEG-PPG-PEG nanoparticles is shown in FIG. 10.

The nanoparticles of the present invention can encapsulate and/or adsorb one or more entities. The entity can also be conjugated to directly to the block copolymer of the biodegradable nanoparticle. Entities of the present invention include but are not limited to, small organic molecules, nucleic acids, polynucleotides, oligonucleotides, nucleosides, DNA, RNA, SiRNA, amino acids, peptides, protein, amines, antibodies and variants thereof, antibiotics, low molecular weight molecules, chemotherapeutics, drugs or therapeutic agents, metal ions, dyes, radioisotope, contrast agent, and/or imaging agents.

Suitable molecules that can be encapsulated are therapeutic agents. Included in therapeutic agents are proteins or peptides or fragments thereof, insulin, etc., hydrophobic drugs like doxorubcin, paclitaxil, gemcetabin, docetaxel etc; antibiotics like amphotericin B, isoniazid (INH) etc, and nucleic acids. Therapeutic agents also include chemotherapeutics such as paclitaxel, doxorubicin pimozide, perimethamine, indenoisoquinolines, or nor-indenoisoquinolines.

The therapeutic agent can comprise natural and non-natural (synthetic) amino acids. Non-limiting examples include bicyclic compounds and peptidomimetics such as cyclic peptidomimetics.

Figure 11A:
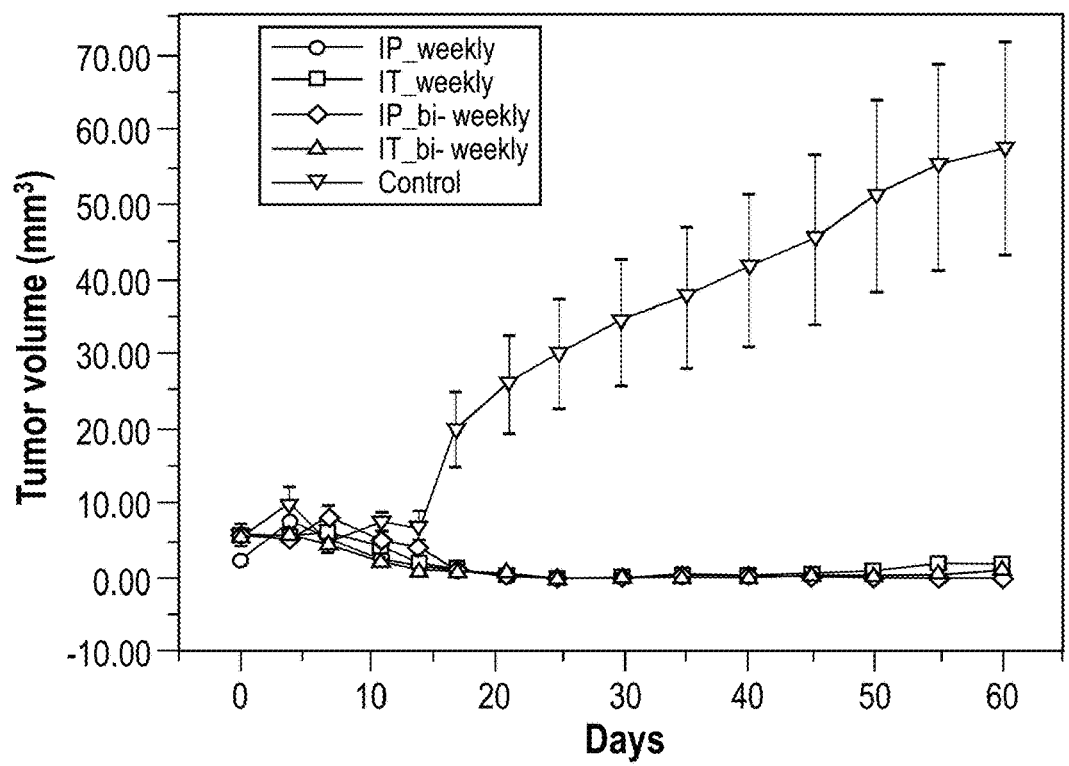
FIGS. 11A and B show tumor regression in Ehrlich Ascites Tumor (EAT) mice treated with L-PLBCL2P9-encapsulated PLA-PEG-PPG-PEG nanoparticles (8,800 g/mol).
Figure 11B:
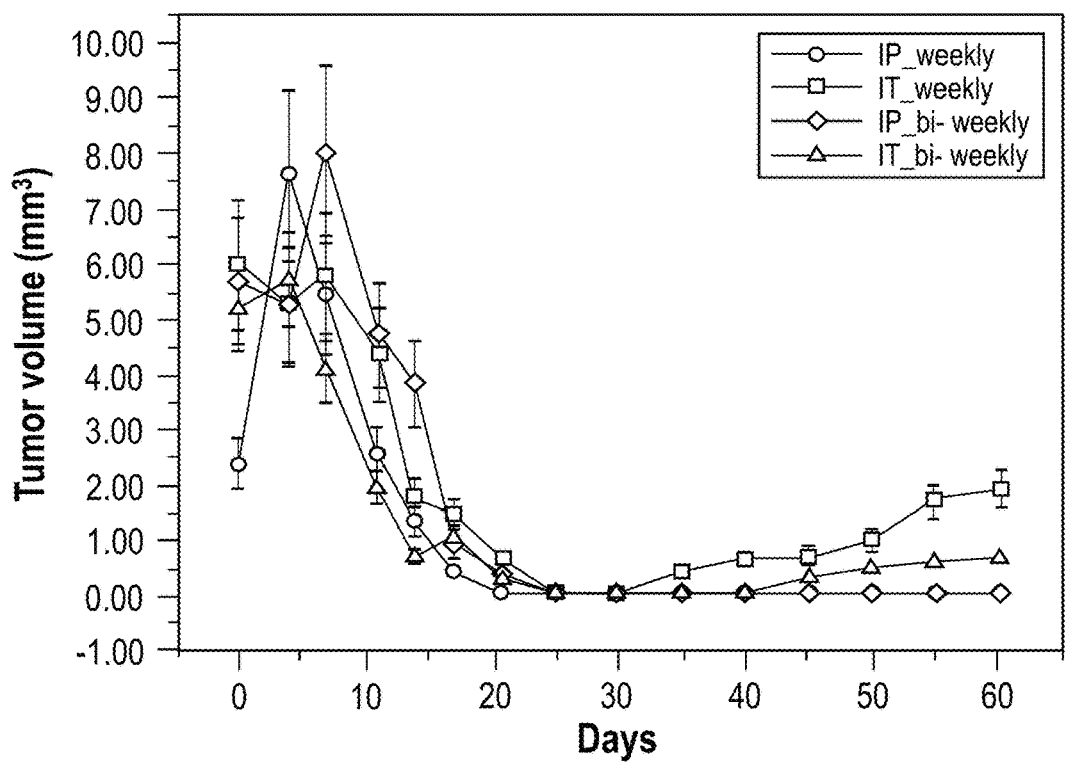
Figure 12C:
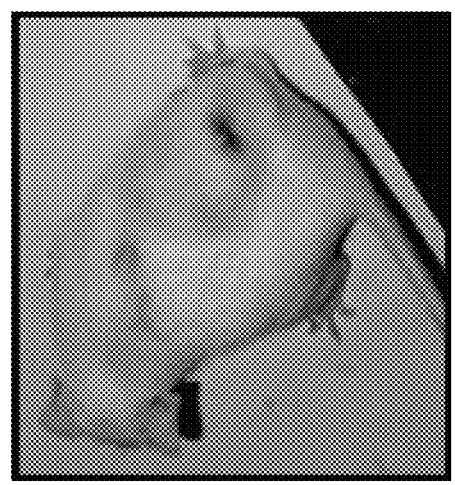
FIG. 12C shows untreated, control mice at day 21.
Figure 12B:
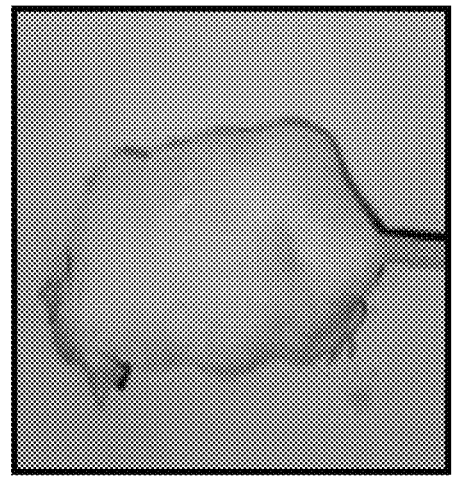
FIG. 12B shows tumor growth suppression in EAT mice treated with PL-BCL2P9-encapsulated PLA-PEG-PPG-PEG nanoparticles (8,800 g/mol) at day 21.
Figure 12A:
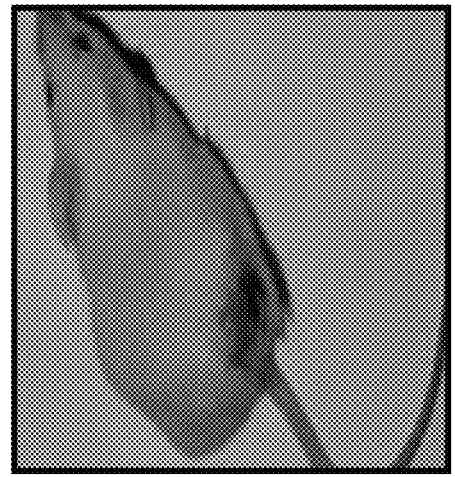
FIG. 12A shows the Ehrlich Ascites Tumor (EAT) mice at day 1.
Figure 13:
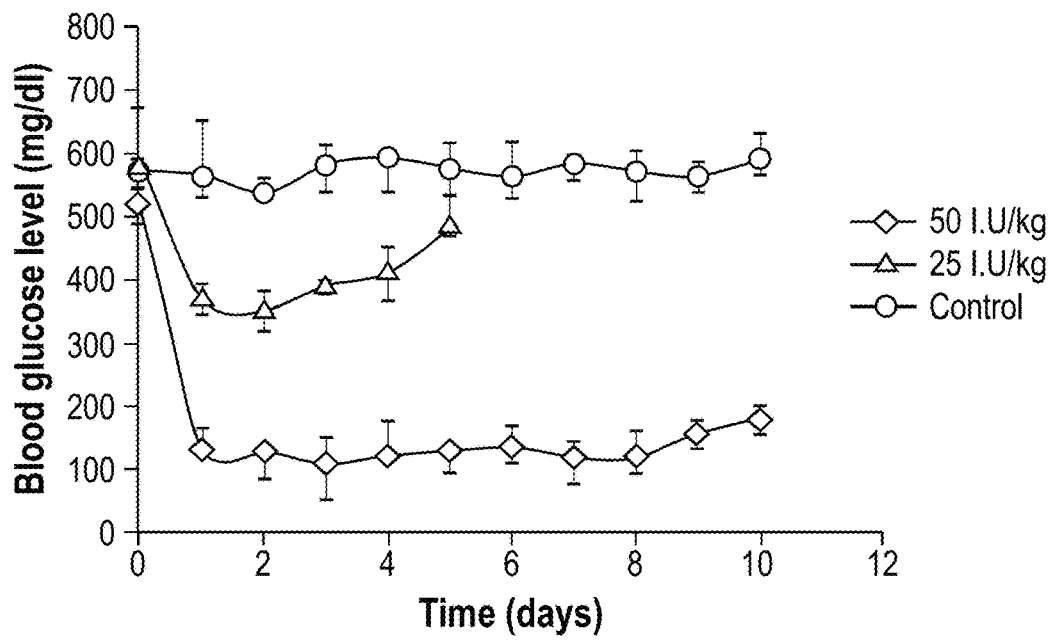
FIG. 13 shows the efficacy of insulin-loaded PLA-PEG-PPG-PEG nanoparticles on controlling blood glucose levels in diabetic rabbits.

It is known that the L-form or L-configuration of the therapeutic peptides are economically cheaper to manufacture but have a disadvantage in drug applications since they are known to degrade very fast in the in-vivo system compared to their D-forms. However, encapsulation of such L-peptides by the nanoparticles of the present invention does not result in degradation in circulation due to encapsulation in the core of the nanoparticles as confirmed by in-vivo studies (FIGS. 11, 12 and 13).

Targeted delivery of the nanoparticles loaded with anticancer drugs can be achieved compared to the free drug formulations prevalent in the art. The nanoparticles of the present invention can also be surface conjugated, bioconjugated, or adsorbed with one or more entities including targeting moieties on the surface of nanoparticles. Targeting moieties cause nanoparticles to localize onto a tumor or a disease site and release a therapeutic agent. The targeting moiety can bind to or associate with a linker molecules. Targeting molecules include but are not limited to antibody molecules, growth receptor ligands, vitamins, peptides, haptens, aptamers, and other targeting molecules known to those skilled in the art. Drug molecules and imaging molecules can also be attached to the targeting moieties on the surface of the nanoparticles directly or via linker molecules.

Specific, non-limiting examples of targeting moieties include vitamins, ligands, amines, peptide fragments, antibodies, aptamers, a transferrin, an antibody or fragment thereof, sialyl Lewis X antigen, hyaluronic acid, mannose derivatives, glucose derivatives, cell specific lectins, galaptin, galectin, lactosylceramide, a steroid derivative, an RGD sequence, EGF, EGF-binding peptide, urokinase receptor binding peptide, a thrombospondin-derived peptide, an albumin derivative and/or a molecule derived from combinatorial chemistry.

Further, the nanoparticles of the present invention may be surface functionalized and/or conjugated to other molecules of interest. Small low molecular weight molecules like folic acid, prostate membrane specific antigen (PSMA), antibodies, aptamers, molecules that bind to receptors or antigens on the cell surface etc, can be covalently bound to the block copolymer PEG-PPG-PEG or the PEG component of the polymeric matrix. In suitable embodiment of the present invention, the matrix comprises of polymer and an entity. In some cases the entity or targeting moiety can be covalently associated with surface of polymeric matrix. Therapeutic agents can be associated with the surface of the polymeric matrix or encapsulated throughout the polymeric matrix of the nanoparticles. Cellular uptake of the conjugated nanoparticle is higher compared to plain nanoparticles.

The nanoparticle of the present invention can comprise one or more agents attached to the surface of nanoparticle via methods well known in the art and also encapsulate one or more agents to function as a multifunctional nanoparticle. The nanoparticles of the present invention can function as multi-functional nanoparticles that can combine tumor targeting, tumor therapy and tumor imaging in an all-in-one system, providing a useful multi-modal approach in the battle against cancer. The multifunctional nanoparticle can have one or more active agents with similar or different mechanisms of actions, similar or different sites of action; or similar and different functions.

Entity encapsulation in the PLA-PEG-PPG-PEG nanoparticle is prepared by emulsion precipitation method. The PLA-PEG-PPG-PEG polymeric nanoparticle prepared using the process of the present invention is dissolved in an organic solvent comprising an organic solvent. The entity is added to the polymeric solution in the weight range of 10-20% weight of the polymer. The polymeric solution is then added drop-wise to the aqueous phase and stirred at room temperature for 10-12 hours to allow for solvent evaporation and nanoparticle stabilization. The entity-loaded nanoparticles are collected by centrifugation, dried, and stored at 2° C.-8° C. until further use. Other additives like sugars, amino acids, methyl cellulose etc., may be added to the aqueous phase in the process for the preparation of the entity-loaded polymeric nanoparticles.

The entity-loading capacity of the nanoparticles of the present invention is high, reaching nearly about 70-90% as shown in Table 3. The PLA-PEG-PPG-PEG based nanocarrier system of the present invention prevents premature degradation and effective and targeted delivery of anticancer peptide to the cancer cells. Surface foliated biodegradable PLA-PEG-PPG-PEG nanoparticles encapsulating therapeutic peptides such as NuBCP-9, Bax BH3 etc., in the core can be effectively delivered into the cytosol of the cancer cells without the use of any cell penetrating peptides. In-vitro studies with MCF-7 cell lines challenged with L-PLBCL2P9-loaded nanoparticles showed complete killing of cells in 48-72 hrs as assessed by XTT assay (FIG. 7B) and in-vivo studies (FIGS. 11 and 12). FIG. 7B also shows the efficacy of the nanoparticles for sustained release and efficient delivery of drug compared with free drug formulations in the MCF-7 cell lines.

In suitable embodiments, higher loading of the entity in the PLA-PEG-PPG-PEG nanoparticles is achieved by linking the active agent with low molecular weight PLA. The entity is covalently linked with low molecular weight PLA by a reaction with a carbodiimide coupling reagent in combination with a hydroxyderivative. As an example, the carbodiimide coupling agent is ethyl-dimethyl aminopropylcarbodiimide and the hydroxyderivative is N-hydroxy-succinimide (EDC/NHS) chemistry. The molecular weight of PLA is in the range of about 3,000-10,000 g/mol. Higher loading of both hydrophobic and hydrophilic drugs in the PLA-PEG-PPG-PEG nanoparticles are achieved (Example 5, Tables 4 and 5). The nanoparticles with encapsulated PLA-drugs were delivered into the cytosol without the aid of cell penetrating peptides (CPPs).

Specific processes for nanoparticle formation and uses in pharmaceutical composition are provided herein for purpose of reference. These processes and uses may be carried out through a variety of methods apparent to those of skill in the art.

Another embodiment of the present invention provides a process for preparation of biodegradable polymeric nanoparticles of PLA-PEG-PPG-PEG block copolymer, wherein said process comprises (a) dissolving a PEG-PPG-PEG copolymer and poly(lactic acid) (PLA) in an organic solvent to obtain a solution (b) adding N,N,-dicyclohexylcarbodiimide (DCC) and 4-(dimethylamino) pyridine (DMAP) to the solution at a temperature in the range of −4° C. to 0° C. to obtain a reaction mixture (c) stirring the reaction mixture at 250 to 400 rpm at a temperature ranging from −4° C. to 0° C. for 20 to 28 hours to obtain the PLA-PEG-PPG-PEG block copolymer (d) dissolving the PLA-PEG-PPG-PEG block copolymer in an organic solvent and homogenizing at 250 to 400 rpm to obtain a homogenized mixture (e) adding the homogenized mixture to an aqueous phase to obtain an emulsion, and (f) stirring the emulsion at 25° C. to 30° C. at 250 to 400 rpm for 10 to 12 hours to obtain the nanoparticles of PLA-PEG-PPG-PEG block copolymer.

In another embodiment of the present invention, there is provided a process for preparation of biodegradable polymeric nanoparticles of PLA-PEG-PPG-PEG block copolymer, wherein said process comprises (a) dissolving a PEG-PPG-PEG copolymer and poly(lactic acid) (PLA) in an organic solvent to obtain a solution (b) adding N,N,-dicyclohexylcarbodiimide (DCC) and 4-(dimethylamino) pyridine (DMAP) to the solution at a temperature in the range of −4° C. to 0° C. to obtain a reaction mixture (c) stirring the reaction mixture at 250 to 400 rpm at a temperature ranging from −4° C. to 0° C. for 20 to 28 hours to obtain the PLA-PEG-PPG-PEG block copolymer (d) dissolving the PLA-PEG-PPG-PEG block copolymer in an organic solvent and homogenizing at 250 to 400 rpm to obtain a homogenized mixture (e) adding the homogenized mixture to an aqueous phase to obtain an emulsion, and (f) stirring the emulsion at 25° C. to 30° C. at 250 to 400 rpm for 10 to 12 hours to obtain the nanoparticles of PLA-PEG-PPG-PEG block copolymer, wherein said process optionally comprises the steps of washing the nanoparticles of PLA-PEG-PPG-PEG block copolymer with water and drying the nanoparticles by conventional method.

In another embodiment of the present invention, there is provided a process for preparation of biodegradable polymeric nanoparticles of PLA-PEG-PPG-PEG block copolymer, wherein said process comprises (a) dissolving a PEG-PPG-PEG copolymer and poly-lactic acid (PLA) in an organic solvent to obtain a solution (b) adding N,N,-dicyclohexylcarbodiimide (DCC) and 4-(dimethylamino) pyridine (DMAP) to the solution at a temperature in the range of −4° C. to 0° C. to obtain a reaction mixture (c) stirring the reaction mixture at 250 to 400 rpm at a temperature ranging from −4° C. to 0° C. for 20 to 28 hours to obtain the PLA-PEG-PPG-PEG block copolymer (d) dissolving the PLA-PEG-PPG-PEG block copolymer in an organic solvent and homogenizing at 250 to 400 rpm to obtain a homogenized mixture (e) adding the homogenized mixture to an aqueous phase to obtain an emulsion, and (f) stirring the emulsion at 25° C. to 30° C. at 250 to 400 rpm for 10 to 12 hours to obtain the nanoparticles of PLA-PEG-PPG-PEG block copolymer, wherein size of the nanoparticle is in the range of 30-120 nm.

In yet another embodiment of the present invention, there is provided a process for preparation of biodegradable polymeric nanoparticles of PLA-PEG-PPG-PEG block copolymer, wherein said process comprises (a) dissolving a PEG-PPG-PEG copolymer and poly-lactic acid (PLA) in an organic solvent to obtain a solution (b) adding N,N,-dicyclohexylcarbodiimide (DCC) and 4-(dimethylamino) pyridine (DMAP) to the solution at a temperature in the range of −4° C. to 0° C. to obtain a reaction mixture (c) stirring the reaction mixture at 250 to 400 rpm at a temperature ranging from −4° C. to 0° C. for 20 to 28 hours to obtain the PLA-PEG-PPG-PEG block copolymer (d) dissolving the PLA-PEG-PPG-PEG block copolymer in an organic solvent and homogenizing at 250 to 400 rpm to obtain a homogenized mixture (e) adding the homogenized mixture to an aqueous phase to obtain an emulsion, and (f) stirring the emulsion at 25° C. to 30° C. at 250 to 400 rpm for 10 to 12 hours to obtain the nanoparticles of PLA-PEG-PPG-PEG block copolymer, wherein molecular weight of the PEG-PPG-PEG copolymer is in the range of 1,000 g/mol to 10,000 g/mol.

In a further embodiment of the present invention, there is provided a process for preparation of biodegradable polymeric nanoparticles of PLA-PEG-PPG-PEG block copolymer, wherein said process comprises (a) dissolving a PEG-PPG-PEG copolymer and poly(lactic acid) (PLA) in an organic solvent to obtain a solution (b) adding N,N,-dicyclohexylcarbodiimide (DCC) and 4-(dimethylamino) pyridine (DMAP) to the solution at a temperature in the range of −4° C. to 0° C. to obtain a reaction mixture (c) stirring the reaction mixture at 250 to 400 rpm at a temperature ranging from −4° C. to 0° C. for 20 to 28 hours to obtain the PLA-PEG-PPG-PEG block copolymer (d) dissolving the PLA-PEG-PPG-PEG block copolymer in an organic solvent and homogenizing at 250 to 400 rpm to obtain a homogenized mixture (e) adding the homogenized mixture to an aqueous phase to obtain an emulsion, and (f) stirring the emulsion at 25° C. to 30° C. at 250 to 400 rpm for 10 to 12 hours to obtain the nanoparticles of PLA-PEG-PPG-PEG block copolymer, wherein molecular weight of PLA is in the range of 10,000 g/mol to 60,000 g/mol.

In a further embodiment of the present invention, there is provided a process for preparation of biodegradable polymeric nanoparticles of PLA-PEG-PPG-PEG block copolymer, wherein said process comprises (a) dissolving a PEG-PPG-PEG copolymer and poly(lactic acid) (PLA) in an organic solvent to obtain a solution (b) adding N,N,-dicyclohexylcarbodiimide (DCC) and 4-(dimethylamino) pyridine (DMAP) to the solution at a temperature in the range of −4° C. to 0° C. to obtain a reaction mixture (c) stirring the reaction mixture at 250 to 400 rpm at a temperature ranging from −4° C. to 0° C. for 20 to 28 hours to obtain the PLA-PEG-PPG-PEG block copolymer (d) dissolving the PLA-PEG-PPG-PEG block copolymer in an organic solvent and homogenizing at 250 to 400 rpm to obtain a homogenized mixture (e) adding the homogenized mixture to an aqueous phase to obtain an emulsion, and (f) stirring the emulsion at 25° C. to 30° C. at 250 to 400 rpm for 10 to 12 hours to obtain the nanoparticles of PLA-PEG-PPG-PEG block copolymer, wherein the solution of step (a) optionally comprises additives such as emulsifier.

Another embodiment of the present invention provides a biodegradable polymeric nanoparticles of PLA-PEG-PPG-PEG block copolymer obtained by the process for preparation of biodegradable polymeric nanoparticles of PLA-PEG-PPG-PEG block copolymer, wherein said process comprises (a) dissolving a PEG-PPG-PEG copolymer and poly(lactic acid) (PLA) in an organic solvent to obtain a solution (b) adding N,N,-dicyclohexylcarbodiimide (DCC) and 4-(dimethylamino) pyridine (DMAP) to the solution at a temperature in the range of −4° C. to 0° C. to obtain a reaction mixture (c) stirring the reaction mixture at 250 to 400 rpm at a temperature ranging from −4° C. to 0° C. for 20 to 28 hours to obtain the PLA-PEG-PPG-PEG block copolymer (d) dissolving the PLA-PEG-PPG-PEG block copolymer in an organic solvent and homogenizing at 250 to 400 rpm to obtain a homogenized mixture (e) adding the homogenized mixture to an aqueous phase to obtain an emulsion, and (f) stirring the emulsion at 25° C. to 30° C. at 250 to 400 rpm for 10 to 12 hours to obtain the nanoparticles of PLA-PEG-PPG-PEG block copolymer.

Another embodiment of the present invention provides a composition comprising the biodegradable polymeric nanoparticle of PLA-PEG-PPG-PEG block copolymer obtained by the process for preparation of biodegradable polymeric nanoparticles of PLA-PEG-PPG-PEG block copolymer, wherein said process comprises (a) dissolving a PEG-PPG-PEG copolymer and poly(lactic acid) (PLA) in an organic solvent to obtain a solution (b) adding N,N,-dicyclohexylcarbodiimide (DCC) and 4-(dimethylamino) pyridine (DMAP) to the solution at a temperature in the range of −4° C. to 0° C. to obtain a reaction mixture (c) stirring the reaction mixture at 250 to 400 rpm at a temperature ranging from −4° C. to 0° C. for 20 to 28 hours to obtain the PLA-PEG-PPG-PEG block copolymer (d) dissolving the PLA-PEG-PPG-PEG block copolymer in an organic solvent and homogenizing at 250 to 400 rpm to obtain a homogenized mixture (e) adding the homogenized mixture to an aqueous phase to obtain an emulsion, and (f) stirring the emulsion at 25° C. to 30° C. at 250 to 400 rpm for 10 to 12 hours to obtain the nanoparticles of PLA-PEG-PPG-PEG block copolymer.

A particular embodiment of the present invention provides a process for preparing biodegradable polymeric nanoparticles of PLA-PEG-PPG-PEG block copolymer comprising at least one entity, wherein said process comprises (a) homogenizing the entity with the polymeric nanoparticles of PLA-PEG-PPG-PEG block copolymer dissolved in an organic solvent at 250 to 400 rpm to obtain a primary emulsion (b) emulsifying the primary emulsion in an aqueous phase at 250 to 400 rpm to obtain a secondary emulsion, and (c) stirring the secondary emulsion at 25° C. to 30° C. at 250 to 400 rpm for 10 to 12 hours to obtain the nanoparticle of PLA-PEG-PPG-PEG comprising the entity.

In another embodiment of the present invention there is provided a process for preparing biodegradable polymeric nanoparticles of PLA-PEG-PPG-PEG block copolymer comprising at least one entity, wherein said process comprises (a) homogenizing the entity with the polymeric nanoparticles of PLA-PEG-PPG-PEG block copolymer dissolved in an organic solvent at 250 to 400 rpm to obtain a primary emulsion (b) emulsifying the primary emulsion in an aqueous phase at 250 to 400 rpm to obtain a secondary emulsion, and (c) stirring the secondary emulsion at 25° C. to 30° C. at 250 to 400 rpm for 10 to 12 hours to obtain the nanoparticle of PLA-PEG-PPG-PEG comprising the entity, wherein said process optionally comprises the steps of washing the nanoparticles of PLA-PEG-PPG-PEG block copolymer comprising the entity with water and drying the nanoparticles by conventional method.

In another embodiment of the present invention there is provided a process for preparing biodegradable polymeric nanoparticles of PLA-PEG-PPG-PEG block copolymer comprising at least one entity, wherein said process comprises (a) homogenizing the entity with the polymeric nanoparticles of PLA-PEG-PPG-PEG block copolymer dissolved in an organic solvent at 250 to 400 rpm to obtain a primary emulsion (b) emulsifying the primary emulsion in an aqueous phase at 250 to 400 rpm to obtain a secondary emulsion, and (c) stirring the secondary emulsion at 25° C. to 30° C. at 250 to 400 rpm for 10 to 12 hours to obtain the nanoparticle of PLA-PEG-PPG-PEG comprising the entity, wherein the entity is selected from a group consisting of small organic molecules, nucleic acids, polynucleotides, oligonucleotides, nucleosides, DNA, RNA, amino acids, peptides, protein, antibiotics, low molecular weight molecules, pharmacologically active molecules, drugs, metal ions, dyes, radioisotopes, contrast agents imaging agents, and targeting moiety.

In another embodiment of the present invention there is provided a process for preparing biodegradable polymeric nanoparticles of PLA-PEG-PPG-PEG block copolymer comprising at least one entity, wherein said process comprises (a) homogenizing the entity with the polymeric nanoparticles of PLA-PEG-PPG-PEG block copolymer dissolved in an organic solvent at 250 to 400 rpm to obtain a primary emulsion (b) emulsifying the primary emulsion in an aqueous phase at 250 to 400 rpm to obtain a secondary emulsion, and (c) stirring the secondary emulsion at 25° C. to 30° C. at 250 to 400 rpm for 10 to 12 hours to obtain the nanoparticle of PLA-PEG-PPG-PEG comprising the entity, wherein the entity is a targeting moiety selected from the group consisting of vitamins, ligands, amines, peptide fragment, antibodies and aptamers.

In another embodiment of the present invention there is provided a process for preparing biodegradable polymeric nanoparticles of PLA-PEG-PPG-PEG block copolymer comprising at least one entity, wherein said process comprises (a) homogenizing the entity with the polymeric nanoparticles of PLA-PEG-PPG-PEG block copolymer dissolved in an organic solvent at 250 to 400 rpm to obtain a primary emulsion (b) emulsifying the primary emulsion in an aqueous phase at 250 to 400 rpm to obtain a secondary emulsion, and (c) stirring the secondary emulsion at 25° C. to 30° C. at 250 to 400 rpm for 10 to 12 hours to obtain the nanoparticle of PLA-PEG-PPG-PEG comprising the entity, wherein the entity is linked to PLA.

In another embodiment of the present invention there is provided a process for preparing biodegradable polymeric nanoparticles of PLA-PEG-PPG-PEG block copolymer comprising at least one entity, wherein said process comprises (a) homogenizing the entity with the polymeric nanoparticles of PLA-PEG-PPG-PEG block copolymer dissolved in an organic solvent at 250 to 400 rpm to obtain a primary emulsion (b) emulsifying the primary emulsion in an aqueous phase at 250 to 400 rpm to obtain a secondary emulsion, and (c) stirring the secondary emulsion at 25° C. to 30° C. at 250 to 400 rpm for 10 to 12 hours to obtain the nanoparticle of PLA-PEG-PPG-PEG comprising the entity, wherein the entity is linked to PLA of molecular weight in the range of 3,000 g/mol to 10,000 g/mol.

Another embodiment of the present invention provides a biodegradable polymeric nanoparticle of PLA-PEG-PPG-PEG comprising at least one entity obtained by the process comprising (a) homogenizing the entity with the polymeric nanoparticles of PLA-PEG-PPG-PEG block copolymer dissolved in an organic solvent at 250 to 400 rpm to obtain a primary emulsion (b) emulsifying the primary emulsion in an aqueous phase at 250 to 400 rpm to obtain a secondary emulsion, and (c) stirring the secondary emulsion at 25° C. to 30° C. at 250 to 400 rpm for 10 to 12 hours to obtain the nanoparticle of PLA-PEG-PPG-PEG comprising the entity.

Another embodiment of the present invention provides a composition comprising the biodegradable polymeric nanoparticle of PLA-PEG-PPG-PEG comprising at least one entity obtained by the process comprising (a) homogenizing the entity with the polymeric nanoparticles of PLA-PEG-PPG-PEG block copolymer dissolved in an organic solvent at 250 to 400 rpm to obtain a primary emulsion (b) emulsifying the primary emulsion in an aqueous phase at 250 to 400 rpm to obtain a secondary emulsion, and (c) stirring the secondary emulsion at 25° C. to 30° C. at 250 to 400 rpm for 10 to 12 hours to obtain the nanoparticle of PLA-PEG-PPG-PEG comprising the entity.

In another embodiment of the present invention, there is provided a composition comprising the biodegradable polymeric nanoparticle of PLA-PEG-PPG-PEG comprising at least one entity obtained by the process comprising (a) homogenizing the entity with the polymeric nanoparticles of PLA-PEG-PPG-PEG block copolymer dissolved in an organic solvent at 250 to 400 rpm to obtain a primary emulsion (b) emulsifying the primary emulsion in an aqueous phase at 250 to 400 rpm to obtain a secondary emulsion, and (c) stirring the secondary emulsion at 25° C. to 30° C. at 250 to 400 rpm for 10 to 12 hours to obtain the nanoparticle of PLA-PEG-PPG-PEG comprising the entity, wherein the composition optionally comprises at least one pharmaceutical excipient selected from the group consisting of preservative, antioxidant, thickening agent, chelating agent, isotonic agent, flavoring agent, sweetening agent, colorant, solubilizer, dye, flavors, binder, emollient, fillers, lubricants and preservative.

Yet another aspect of the present invention provides a method for treating disease comprising administering biodegradable polymeric nanoparticles of PLA-PEG-PPG-PEG further comprising at least one therapeutic agent, to a subject in need thereof.

In another aspect, the present invention provides for the use of the biodegradable polymeric nanoparticle made up of PLA-PEG-PPG-PEG block copolymer comprising at least one entity for the manufacture of a medicament.

Also provided herein are pharmaceutical compositions or formulations, comprising the nanoparticles provided herein and a pharmaceutically acceptable carrier or excipient.

Suitable pharmaceutical formulations can contain, for example, from about 0.1% to about 99.9%, preferably from about 1% to about 60%, of the active ingredient(s). Pharmaceutical formulations for enteral or parenteral administration are, for example, those in unit dosage forms, such as sugar-coated tablets, tablets, capsules or suppositories, or ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount may be reached by administration of a plurality of dosage units.

The pharmaceutical compositions can contain, as the active ingredient, one or more of the nanoparticles of the invention in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose (e.g. lactose monohydrate), dextrose, sucrose, sorbitol, mannitol, starches (e.g. sodium starch glycolate), gum acacia, calcium phosphate, alginates, tragacanth, gelatin, calcium silicate, colloidal silicon dioxide, microcrystalline cellulose, polyvinylpyrrolidone (e.g. povidone), cellulose, water, syrup, methyl cellulose, and hydroxypropyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Although the subject matter has been described in considerable detail with reference to certain preferred embodiments thereof, other embodiments are possible. As such, the spirit and scope of the appended claims should not be limited to the description of the preferred embodiment contained therein.

EXAMPLES

The disclosure will now be illustrated with working examples, and which is intended to illustrate the working of disclosure and not intended to restrictively any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Example 1

Preparation of Polymeric Nanoparticles of PLA-PEG-PPG-PEG Block Copolymer

Poly(lactic acid) (Mw. ~45,000-60,000 g/mol), PEG-PPG-PEG (Table 1) and tissue culture reagents were obtained from Sigma-Aldrich (St. Louis, Mo.). All reagents were analytical grade or above and used as received, unless otherwise stated. Cell lines were obtained from NCCS Pune, India. Nur-9 peptide was custom synthesized with 95% purity.

Preparation of PLA-PEG-PPG-PEG Block Copolymer 5 gm of poly (lactic acid) (PLA) with an average molecular weight of 60,000 g/mol was dissolved in 100 ml $CH_2Cl_2$ (dichloromethane) in a 250 ml round bottom flask. To this solution, 0.7 g of PEG-PPG-PEG polymer (molecular weight range of 1100-8400 Mn) was added. The solution was stirred for 10-12 hours at 0° C. To this reaction mixture, 5 ml of 1% N,N-dicyclohexylcarbodiimide (DCC) solution was added followed by slow addition of 5 ml of 0.1% 4-Dimethylaminopyridine (DMAP) at −4° C. to 0° C./sub zero temperatures. The reaction mixture was stirred for the next 24 hours followed by precipitation of the PLA-PEG-PPG-PEG block copolymer with diethyl ether and filtration using Whatman filter paper No. 1. The PLA-PEG-PPG-PEG block copolymer precipitates so obtained are dried under low vacuum and stored at 2° C. to 8° C. until further use.

Preparation of PLA-PEG-PPG-PEG Nanoparticles

The PLA-PEG-PPG-PEG nanoparticles were prepared by emulsion precipitation method. 100 mg of the PLA-PEG-PPG-PEG copolymer obtained by the above mentioned process was separately dissolved in an organic solvent, for example, acetonitrile, dimethyl formamide (DMF) or dichloromethane to obtain a polymeric solution.

The nanoparticles were prepared by adding this polymeric solution drop wise to the aqueous phase of 20 ml distilled water. The solution was stirred magnetically at room temperature for 10 to 12 hours to allow residual solvent evaporation and stabilization of the nanoparticles. The nanoparticles were then collected by centrifugation at 25,000 rpm for 10 min and washed thrice using distilled water. The nanoparticles were further lyophilized and stored at 2° C. to 8° C. until further use.

Characterization of Polymeric Nanoparticles of PLA-PEG-PPG-PEG Block Copolymer

The shape of the nanoparticles obtained by the process mentioned above is essentially spherical as is seen in the Transmission Electron Microscopy Image shown in FIGS.

4A-B. The TEM images allowed for the determination of the particle size range, which is about 30 to 120 nm. The hydrodynamic radius of the nanoparticle was measured using a dynamic light scattering (DLS) instrument and is in the range of 110-120 nm (Table 2).

The characteristics of the PLA-PEG-PPG-PEG nanoparticles synthesized using a range of molecular weights of the block copolymer, PEG-PPG-PEG, is shown in Table 2. The FTIR spectra of the PLA, PLA-PEG, the block copolymer PEG-PPG-PEG and the polymeric nanoparticles PLA-PEG-PPG-PEG are given in FIG. 2A. The FTIR proved to be insensitive to the differences between these species. Therefore, further characterization was done using NMR.

Figure 3A:
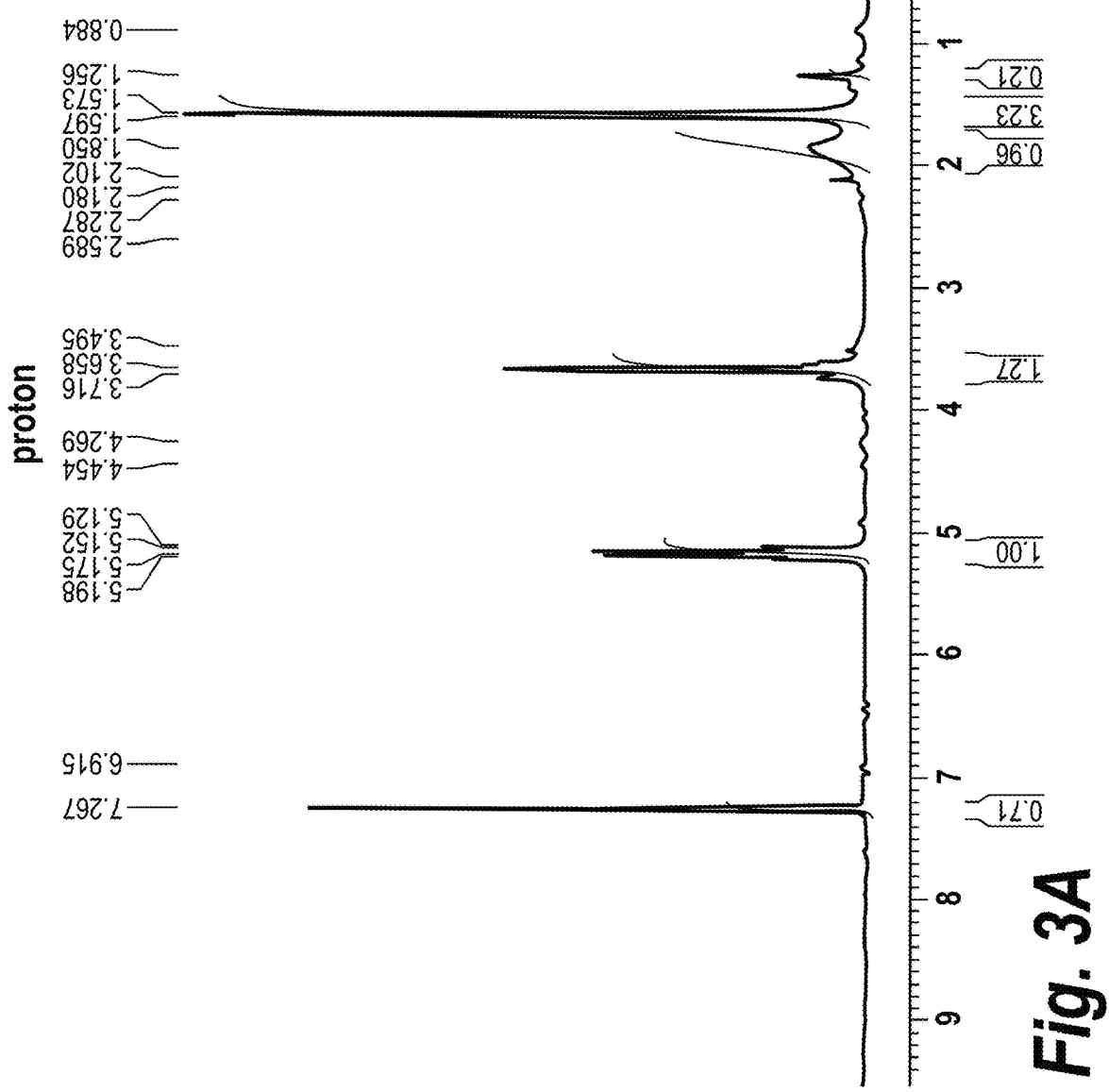
FIG. 3A shows the Nuclear Magnetic Resonance (NMR) spectra of PLA-PEG-PPG-PEG nanoparticles synthesized from a block copolymer of PEG-PPG-PEG of 1,100 g/mol.
Figure 3B:
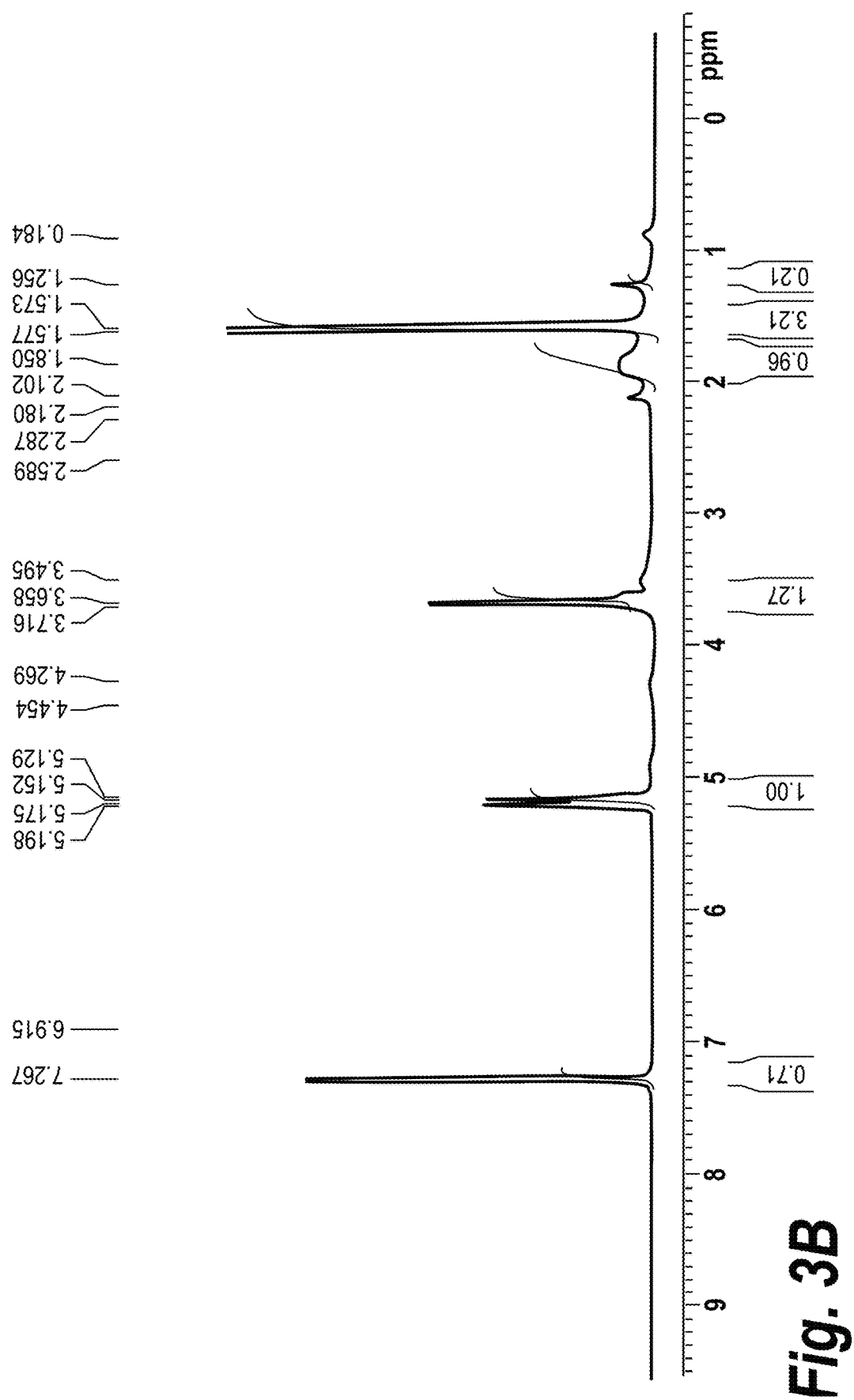
FIG. 3B shows the Nuclear Magnetic Resonance (NMR) spectra of PLA-PEG-PPG-PEG nanoparticles synthesized from a block copolymer of PEG-PPG-PEG of 4,400 g/mol.
Figure 3C:
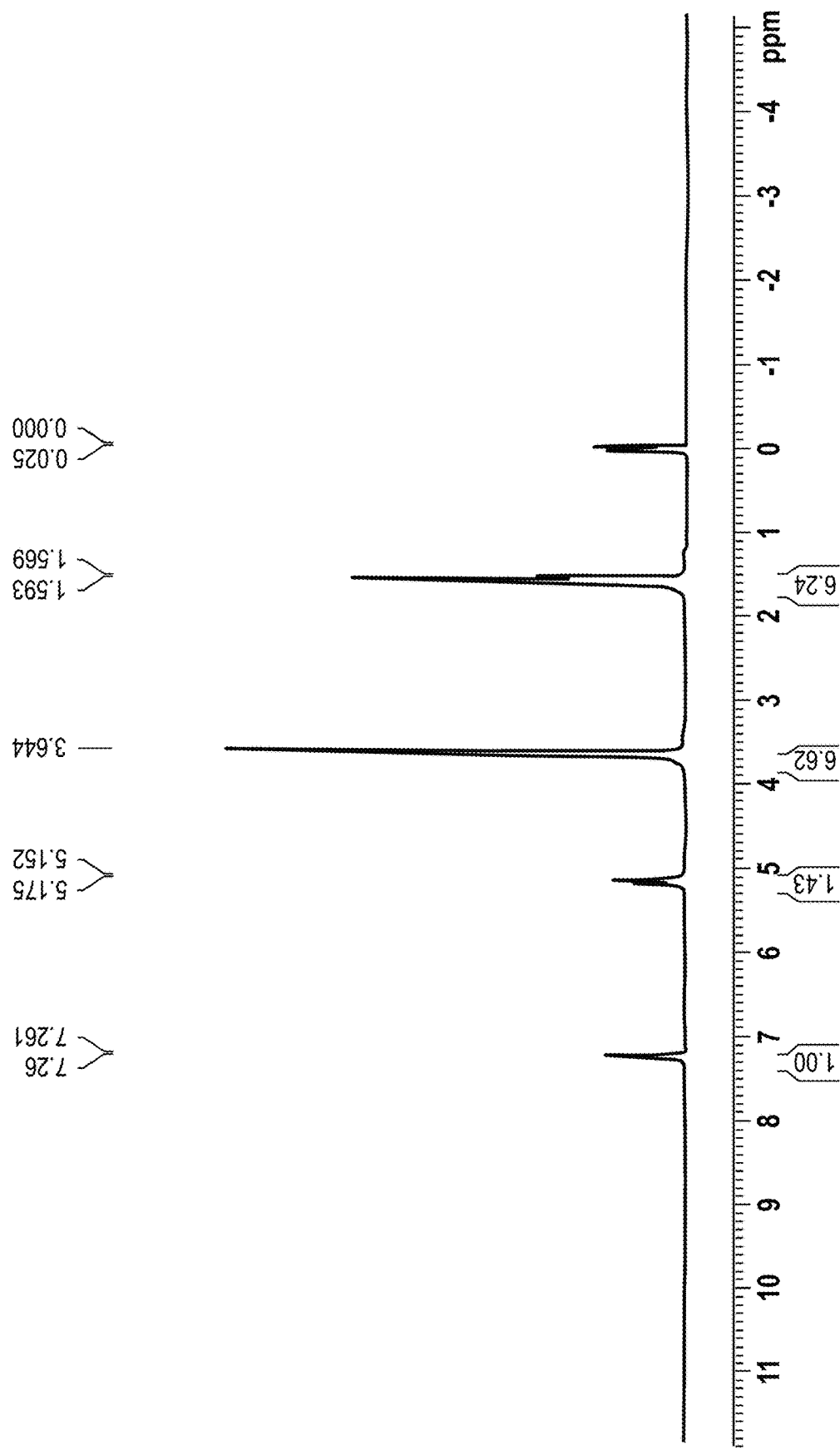
FIG. 3C shows the Nuclear Magnetic Resonance (NMR) spectra of PLA-PEG-PPG-PEG nanoparticles synthesized from a block copolymer of PEG-PPG-PEG of 8,400 g/mol.
Figure 4A:
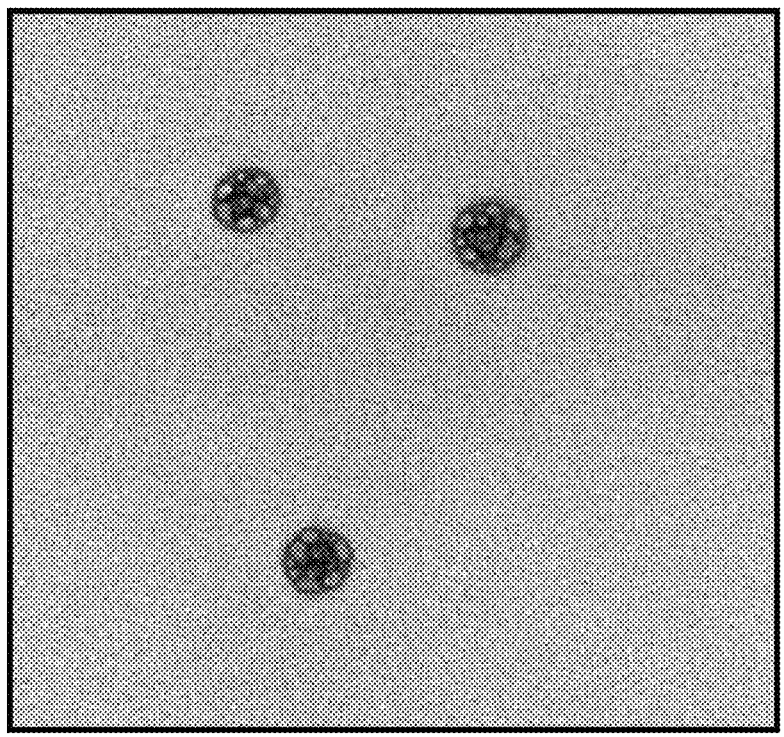
FIGS. 4A and B show Transmission Electron Micrograph (TEM) images of PLA-PEG-PPG-PEG polymeric nanoparticles.
Figure 4B:
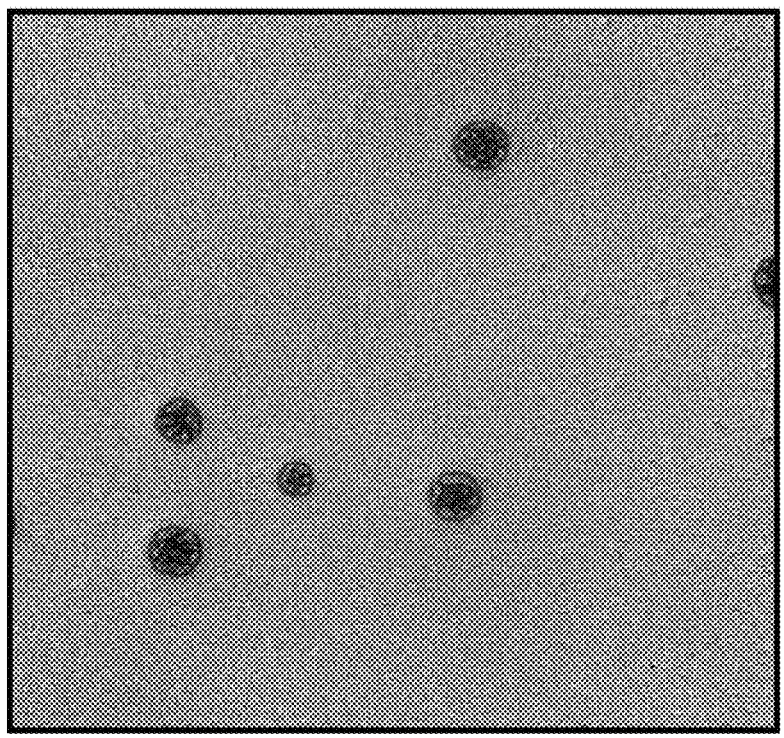

The NMR spectra of the PLA-PEG-PPG-PEG nanoparticles obtained using different molecular weights of the block copolymer, PEG-PPG-PEG, are shown in FIGS. 3A-C. In the figures, the proton with a chemical shift of about 5.1 represents the ester proton of PLA and the proton with a chemical shift at around 3.5 represent the ether proton of PEG-PPG-PEG. The presence of both the protons in the spectra confirms the conjugation of PLA with PEG-PPG-PEG.

Example 2

Preparation of an Entity-Encapsulated Nanoparticle
Preparation of a Drug Encapsulated Polymeric Nanoparticle The nanoparticles of the present invention are amphiphillic in nature and are capable of being loaded with both hydrophobic drugs like Doxorubicin and hydrophilic drugs like the anticancer nine mer peptides, (L-NuBCP-9 or L-PLBCL2P9, L-configuration of FSRSLHSLL (SEQ ID NO:1)), 16 mer-BH3 domain etc.

100 g of the PLA-PEG-PPG-PEG nanoparticle prepared using the process of Example 1 is dissolved in 5 ml of an organic solvent like acetonitrile ($CH_3CN$), dimethyl formamide (DMF; $C_3H_7NO$), acetone or dichloromethane ($CH_2Cl_2$).

1-5 mg of the drug entity, L-PLBCL2P9 (L-configuration of FSRSLHSLL (SEQ ID NO:1)), is dissolved in an aqueous solution and is added to the above polymeric solution. The entity is usually taken in the weight range of about 10-20% weight of the polymer. This solution is briefly sonicated for 10-15 seconds at 250-400 rpm produce a fine primary emulsion.

The fine primary emulsion is added drop wise using a syringe/micropipette to the aqueous phase of 20 ml distilled water and stirred magnetically at 250 to 400 rpm at 25° C. to 30° C. for 10 to 12 h in order to allow solvent evaporation and nanoparticle stabilization. The aqueous phase further comprises a sugar additive. The resulting nanoparticle suspension was allowed to stir overnight, in an open, uncovered condition to evaporate the residual organic solvent. The L-PLBCL2P9 encapsulated polymeric nanoparticles are collected by centrifugation at 10,000 g for 10 min or by ultrafiltration at 3000 g for 15 min. (Amicon Ultra, Ultracel membrane with 100,000 NMWL, Millipore, USA). The nanoparticles are resuspended in distilled water, washed thrice and lyophilized. They are stored at 2° C. to 8° C. until further use. The polymeric nanoparticles are highly stable with no stealth character.

Comparison of the Loading Efficacy of the Polymeric Nanoparticle Prepared Using Different Weights of the Co-Polymer PLA-PEG-PPG-PEG polymeric nanoparticles were prepared using different molecular weights of the PEG-PPG-PEG polymer using the process as mentioned above. Pyrene loaded PLA-PEG-PPG-PEG polymeric nanoparticles were prepared using the PLA-PEG-PPG-PEG copolymer synthesized using varying molecular weights of the PEG-PPG-PEG polymer. Pyrene was taken in the range of 2-20% weight of the PLA-PEG-PPG-PEG block copolymer and fluorescent dye-loaded nanoparticles were prepared. The entity loading capacity of the nanoparticles varied depending on the molecular weight of the PEG-PPG-PEG polymer used for the synthesis of the nanoparticles. Table 3 provides the percentage of the imaging molecule encapsulated by the polymeric nanoparticles produced using different molecular weights of the block copolymer.

Cellular Internalization of the Fluorescent Dye, Rhodamine

Rhodamine loaded PLA-PEG-PPG-PEG polymeric nanoparticles were prepared using the process as mentioned above. Rhodamine was taken in the range of 2-20% weight of the PLA-PEG-PPG-PEG block copolymer and fluorescent dye-loaded nanoparticles were prepared. $1 \times 10^5$ MCF-7 cells were initially plated and grown to 60% confluence on cover slip flasks. Cells were then washed twice with phosphate-buffered saline (PBS) and cultured in 10 ml of DMEM medium containing 10% Foetal Bovine Serum (FBS) and 1% penicillin/streptomycin for 24 h. The growth medium was then aspirated and the cells were washed twice with PBS. The rhodamine-loaded nanoparticles were added to cells attached to coverslips and incubated at 37° C. for 12 hrs. After incubation, cells were washed, and coverslips were removed. This was followed by washing with PBS solution and finally fixed with 4% paraformaldehyde for 20 minutes at room temperature. After removing the fixing agent, the cells were washed and cells were stain with DAPI (florescent dye-stain nuclei cells) for 5 min and then rinsed in running tap water for 1 min. The coverslips were then analyzed using confocal fluorescent microscope (Olympus, Fluoview FV1000 Microscope, Japan). Cellular internalization of nanoparticles in MCF-7 cells was confirmed by using fluorescent dye (Rhodamine B) loaded nanoparticles in conjunction with Confocal Laser Scanning Microscope (CLSM) (FIG. 5).

Example 3

Preparation of Drug Encapsulated Polymeric Nanoparticle with a Targeting Moiety

Various small molecules like amines or amino acids which provide a —COOH or —$NH_2$ functionality, respectively, may be used for conjugation of biomolecules as targeting moieties onto the polymeric nanoparticles of the present invention.

Preparation of PLA-PEG-PPG-PEG-Lysine

PLA-PEG-PPG-PEG copolymer was conjugated to amino acid, lysine, to have —$NH_2$ group. 5 g of PLA-PEG-PPG-PEG and 0.05 g of lysine were dissolved in 100 ml acetonitrile/dichloromethane (1:1) in 250 ml RB flask and allowed to stir at −4-0° C. To this solution, 1% N,N-Dicyclohexylcarbodiimide (DCC) solution was added followed by slow addition of 0.1% 4-Dimethylaminopyridine (DMAP) at 0° C. The reaction mixture was stirred for 24 hours after which PLA-PEG-PPG-PEG-Lysine was precipitated by diethyl ether and filtered through Whatman filter paper No. 1. Precipitates were dried under low vacuum and kept at 2-8° C. until further use.

Preparation of Nanoparticles from PLA-PEG-PPG-PEG-Lysine

For nanoparticles preparation, PLA-PEG-PPG-PEG-Lysine copolymer (100 mg) was dissolved in acetonitrile (or dimethyl formamide (DMF) or dichloromethane). Drug (about 10-20% weight of the polymer) was then added to the solution with brief sonication of 15 s to produce a primary emulsion. The resulting primary emulsion was added dropwise to the aqueous phase of distilled water (20 ml) and stirred magnetically at room temperature for 10-12 hrs in order to allow solvent evaporation and nanoparticle stabilization. The formed nanoparticles were collected by centrifugation at 25,000 rpm for 10 min and washed thrice using distilled water and lyophilized followed by storage at 2-8° C. for further use.

Bio-Conjugation of Nanoparticles with Folic Acid (FA)

20 mg of lyophilized PLA-PEG-PPG-PEG nanoparticles were dissolved in milliQ water and were treated with N-(3-diethylaminopropyl)-N-ethylcarbodiimide (EDC)(50 µl, 400 mM) and N-hydroxysuccinamide (NHS) (50 µl, 100 mM) and the mixture was gently shaken for 20 min. After this folic acid solution of 10 mM was added and the solution was gently shaken for 30 minutes followed by filtration using an amikon filter to remove un-reacted FA which remains in the filtrate. Folic acid conjugated nanoparticles were lyophilized followed by storage at −20° C.

Example 4

Evaluation of the Delivery Potential of the PLA-PEG-PPG-PEG Polymeric Nanoparticle
In-Vitro Release of Encapsulated Drug by the Polymeric Nanoparticle PLA-PEG-PPG-PEG A mixture containing 10 ml phosphate buffer saline and 10 mg PLA-PEG-PPG-PEG nanoparticles encapsulating rhodamine B-conjugated L-PLBCL2P9 (drug) was stirred at 200 rpm at 37° C. Supernatant samples of the mixture were collected by centrifugation at 25,000 rpm at different time intervals for a period of 6 days. The nanoparticles were re-suspended in fresh buffer after each centrifugation. 2 ml of the supernatant was subjected to protein estimation using BCA kit (Pierce, USA) to evaluate the amount of drug release spectrophotometrically at 562 nm. The drug release was calculated by means of a standard calibration curve. It was observed that the release of the drug by the PLA-PEG-PPG-PEG polymeric nanoparticles can be controlled better than the conventional PLA nanoparticles (FIG. 6A).

Figure 6B:
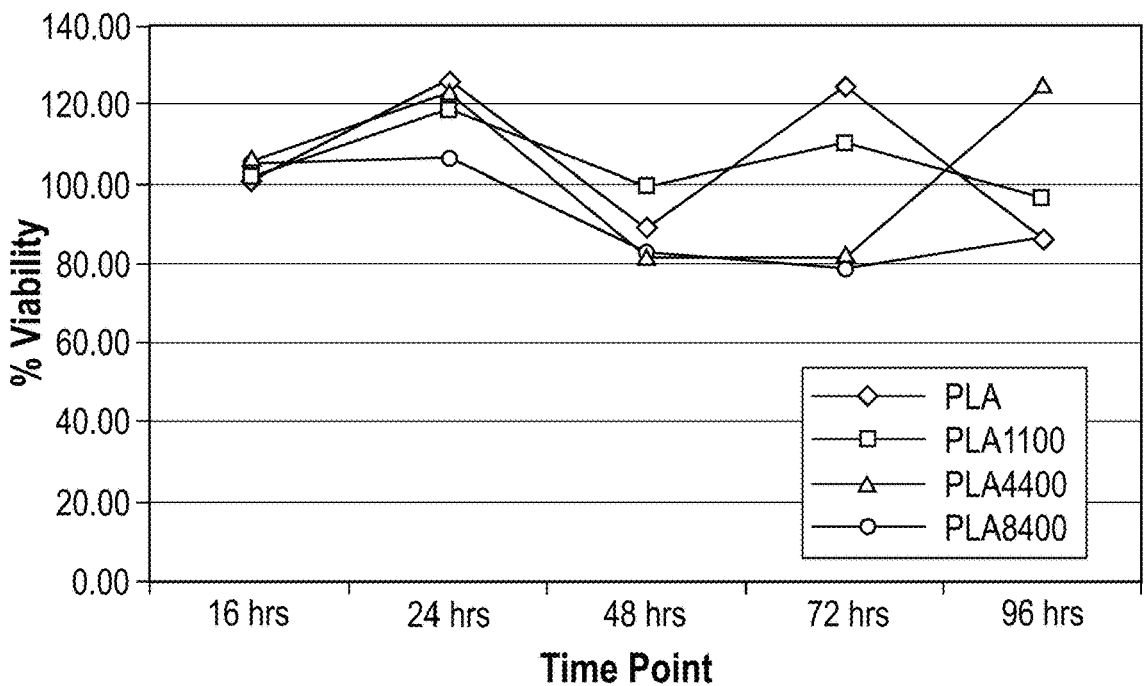
FIG. 6B shows the efficacy of PLA-PEG-PPG-PEG nanoparticles synthesized using different block copolymers loaded with L-PLBCL2P9 drug release and cell proliferation in MCF-7 cell line.
Figure 7A:
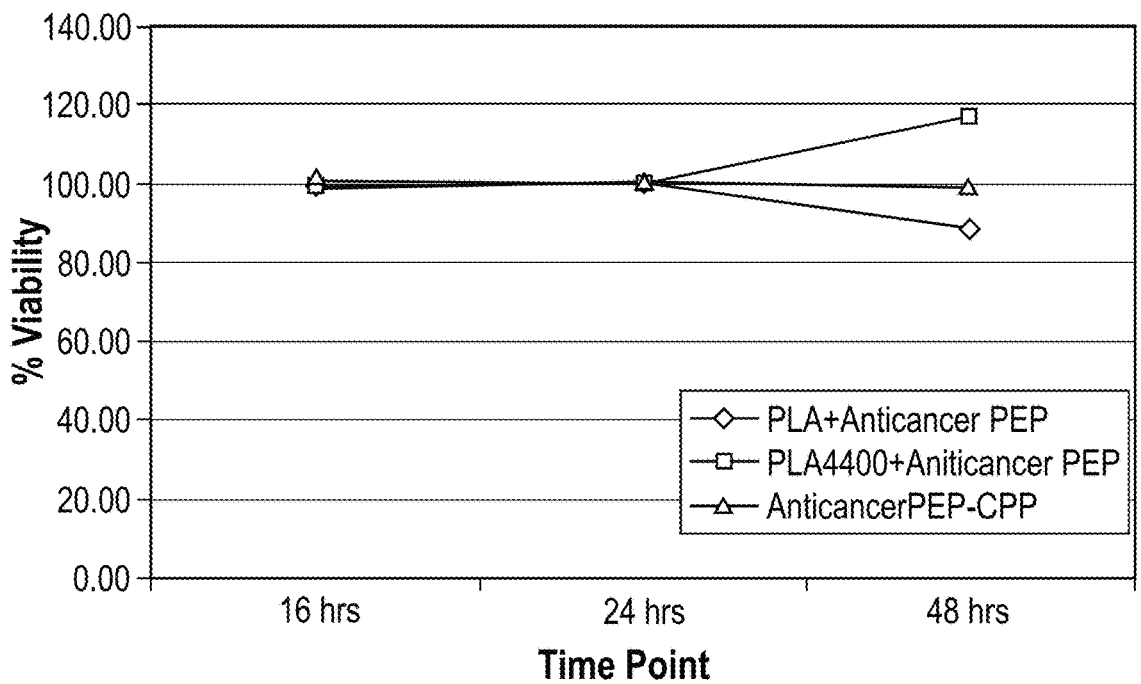
FIG. 7A shows the efficacy of the anticancer peptide, L-PLBCL2P9-loaded PLA-PEG-PPG-PEG nanoparticles on Primary HUVEC cell line.
Figure 7B:
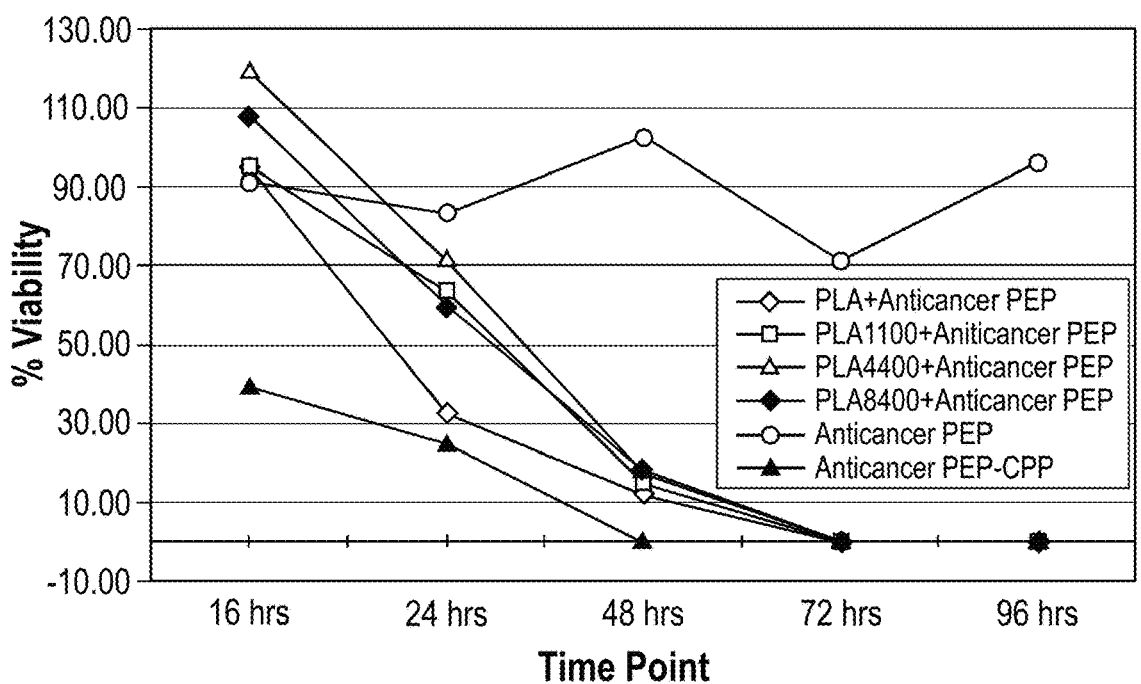
FIG. 7B shows the efficacy of the delivery of the PLA-PEG-PPG-PEG nanoparticles loaded with anticancer peptide, L-PLBCL2P9, compared with drug delivery using cell penetrating peptide (CPP) on MCF-7 cell proliferation.

The XTT (Sodium 2,3,-bis(2-methoxy-4-nitro-5-sulfophenyl)-5-[(phenylamino)-carbonyl]-2H-tetrazolium Inner Salt) Assay Cell viability using XTT (sodium 2,3,-bis(2-methoxy-4-nitro-5-sulfophenyl)-5-[(phenylamino)-carbonyl]-2H-tetrazolium inner salt) assays were carried out in Primary HUVEC cell lines and the MCF-7 cell lines (FIGS. 6B, 7A and 7B).

A total of $1 \times 10^4$ MCF-7 cells were seeded on each well of a 96-well plate and cultured for 24 h. After 24 hours, cells in each plate were treated with polymeric nanoparticles of the present invention containing 5 µM L-PLBCL2P9 peptide or control nanoparticles without any peptide. Cells were also separately treated with the same concentration of L-PLBCL2P9 peptide without any cell penetrating peptide (CPP). The cells were incubated with the nanoparticles for different intervals of time ranging from 16 h, 24 h, 48 h, 72 h and 96 h. After incubation, the medium containing PLA-PEG-PPG-PEG nanoparticles loaded with anticancer peptide—L-PLBCL2P9 was exchanged with fresh medium, and 10 µl of the reconstitute XTT mixture kit reagent were added to each well. After culturing for 4 h, the absorbance of the sample was measured by using a microtiter plate reader (Bio-Rad, CA, U.S.A.) at 450 nm. The proliferation of cells was determined as the percentage of viable cells of the untreated control and analyzed in triplicate. FIG. 6B shows the effect of L-PLBCL2P9-loaded PLA-PEG-PPG-PEG nanoparticle on the cell viability of MCF-7 cell line in relation to time. FIG. 7A shows the effect of the drug L-PLBCL2P9 loaded PLA-PEG-PPG-PEG nanoparticle on the cell viability of Primary HUVEC cell line in relation to time.

Example 5

Modification of Peptide Drugs to Achieve Higher Therapeutic Loading in Nanoparticles Higher loading of hydrophobic as well as hydrophilic therapeutic agents was achieved by covalently modifying the drug moiety with low molecular weight PLA. The peptide drug is modified using low molecular weight of PLA using ethyl-dimethyl aminopropylcarbodiimide and N-hydroxy-succinimide (EDC/NHS) chemistry. The average molecular weight of the PLA used for linking the entity is usually in the range of about 3,000-10,000 g/mol.

1 g of PLA having molecular weight of 5,000 g/mol was dissolved in 10 ml acetonitrile. To this solution, 500 µl of N-(3-diethylaminopropyl)-N-ethylcarbodimide (EDC; 400 mM) in dichloromethane and 500 µl N-hydroxysuccinamide (NHS; 100 mM) in dichloromethane was added. The mixture was gently shaken for 2 hours followed by precipitation of PLA with diethyl ether. This PLA was termed "activated" PLA. 1 mmol of activated PLA was dissolved in acetonitrile and to this solution, 1 mmol of peptide drug L-PLBCL2P9, was added and the reaction mixture was gently shaken again for 30 min. This mixture was then precipitated with diethyl ether and dried under low vacuum followed by storage at −20° C. until further use.

The drug loading capacity of the polymeric nanoparticle increased with an increase in the weight of the block copolymer used for the preparation of the nanoparticle. The drug loading capacity of the nanoparticle is also significantly increased by the conjugation of the low molecular weight PLA with the therapeutic agent (i.e. L-PLBCL2P9) prior to the loading of the drug into the polymeric nanoparticles, as shown in Tables 4 and 5. The increase in the drug loading capacity of the nanoparticles of the present invention is by 5% to 10%.

Example 6

In Vivo Studies to Evaluate the Safety and Toxicity of the Nanoparticles

Studies were conducted in BALB/c mice to evaluate the toxicity and safety of the PLA-PEG-PPG-PEG polymeric nanoparticles prepared using the process as given in Example 1.

Hematology Parameters

PLA-PEG-PPG-PEG nanoparticles were intravenously injected in the animal group at a single dose of 150 mg/kg body weight and hematology parameters were evaluated in the control and nanoparticle-treated groups at intervals of 7 days for a period of 21 days. The control group received no nanoparticles.

There was no significant change in the Complete Blood Count (CBC), Red blood cell (RBC) count, White blood cell (WBC) count, Neutrophils, lymphocytes, packed cell volume, MCV (Mean Corpuscular Volume), MCH (Mean Corpuscular Hemoglobin) and MCHC (Mean Corpuscular Hemoglobin Concentration) between the control and the nanoparticle-treated groups as seen in FIG. 8.

Biochemistry Blood Assays for Liver and Kidney Functions

PLA-PEG-PPG-PEG nanoparticles were intravenously injected in the animal group at a single dose of 150 mg/kg body weight and hematology parameters were evaluated in the control and nanoparticle-treated groups at intervals of 7 days for a period of 21 days.

There were no significant changes in the total protein, albumin and globulin levels between the control and the treated groups. The levels of the liver enzymes, alanine transaminase (ALT), aspartate transaminase (AST) and alkaline phosphatase (ALP) were non-significantly increased in the PLA-PEG-PPG-PEG nanoparticle treated group as seen in FIG. 9. Urea and Blood urea nitrogen (BUN) is a good indicator of renal function. There was no significant change in the urea and BUN levels of treated mice compared to control as seen in FIG. 9.

Histopathology of the Organs of Mice Treated with PLA-PEG-PPG-PEG Nanoparticles

BALB/c mice were treated with PLA-PEG-PPG-PEG nanoparticles at a single dose of 150 mg/kg body weight. After 21 days, the animals were sacrificed and histology of the organ tissues was carried out to assess any tissue damage, inflammation, or lesions due to toxicity caused by the PLA-PEG-PPG-PEG nanoparticles or their degradation products. No apparent histopathological abnormalities or lesions were observed in the brain, heart, liver, spleen, lung and kidney of the nanoparticle-treated animal, as shown in FIG. 10.

Example 7

Efficacy of the PLA-PEG-PPG-PEG Nanoparticles as Nanocarrier Systems In-Vivo

Ehrlich Ascites Tumor (EAT) model transgenic mice of strain BALB/c type were used for evaluating the efficacy of the nanoparticles as nanocarrier systems. Animals having body weight of 20 g were taken up for the study (FIG. 12a).

Anticancer peptide drug, L-PLBCL2P9, was loaded into the PLA-PEG-PPG-PEG polymeric nanoparticles. The mice were given an intraperitoneal formulation of the polymeric nanoparticles as prepared in Example 2 comprising the anticancer peptide, L-PLBCL2P9, at a dose of 200-1000 μg of peptide encapsulated in PLA-PEG-PPG-PEG. The total weight of the anticancer peptide given to the animals was 300 μg to 600 μg/mice. The dosing frequency of the formulation was biweekly for a period of 21 days and the animals were kept under observation for a period of 60 days.

Tumor growth suppression was observed in the mice after administration of the nanoparticles loaded with L-PLBCL2P9 for a period of 60 days (FIG. 11). It was found that the mice treated with the L-PLBCL2P9-loaded nanoparticles were completely cured of tumor (FIG. 12b) compared to the control group (FIG. 12c). The control group received plain nanoparticles without any therapeutic agent.

Evaluation of Insulin Loaded PLA-PEG-PPG-PEG Nanoparticles as Parenteral Depot in Diabetic Rabbits Encapsulation of Insulin in PLA-PEG-PPG-PEG Nanoparticles Insulin encapsulated PLA-PEG-PPG-PEG nanoparticles were prepared by the double emulsion solvent evaporation method. For nanoparticle preparation, 1 g of PLA-PEG-PPG-PEG copolymer was dissolved in acetonitrile. Insulin (500 I.U.) was added to the solution with brief sonication of 15 s to produce a primary emulsion. The resultant primary emulsion was added drop-wise to 30 ml aqueous phase and stirred magnetically at room temperature for 6-8 hours in order to allow solvent evaporation and nanoparticle stabilization. The nanoparticles were collected by centrifugation at 21,000 rpm for 10 min and washed thrice using distilled water. The insulin loaded-PLA-PEG-PPG-PEG nanoparticles were lyophilized and stored at 4° C. until further use.

In-Vivo Studies

Diabetic rabbits were administered a single dose of 50 I.U./kg body weight insulin loaded PLA-PEG-PPG-PEG nanoparticles, subcutaneously, and monitored for 10 days.

In animals given an insulin dose of 50 I.U./kg body weight, the blood glucose level was maintained between 120-150 mg/dl up to 8 days after which a gradual increase in blood glucose level was observed. The drug loaded polymeric nanoparticles form a depot at the site of injection and release the entrapped insulin in a sustained manner due to slow degradation and diffusion. The glucose level did not revert to original diabetic levels (500 mg/dl) even after 8 days, indicating the capability of polymeric nanoparticles to hold and release bioactive insulin in a sustained manner for more than a one week time period (FIG. 13).

Figure 14:
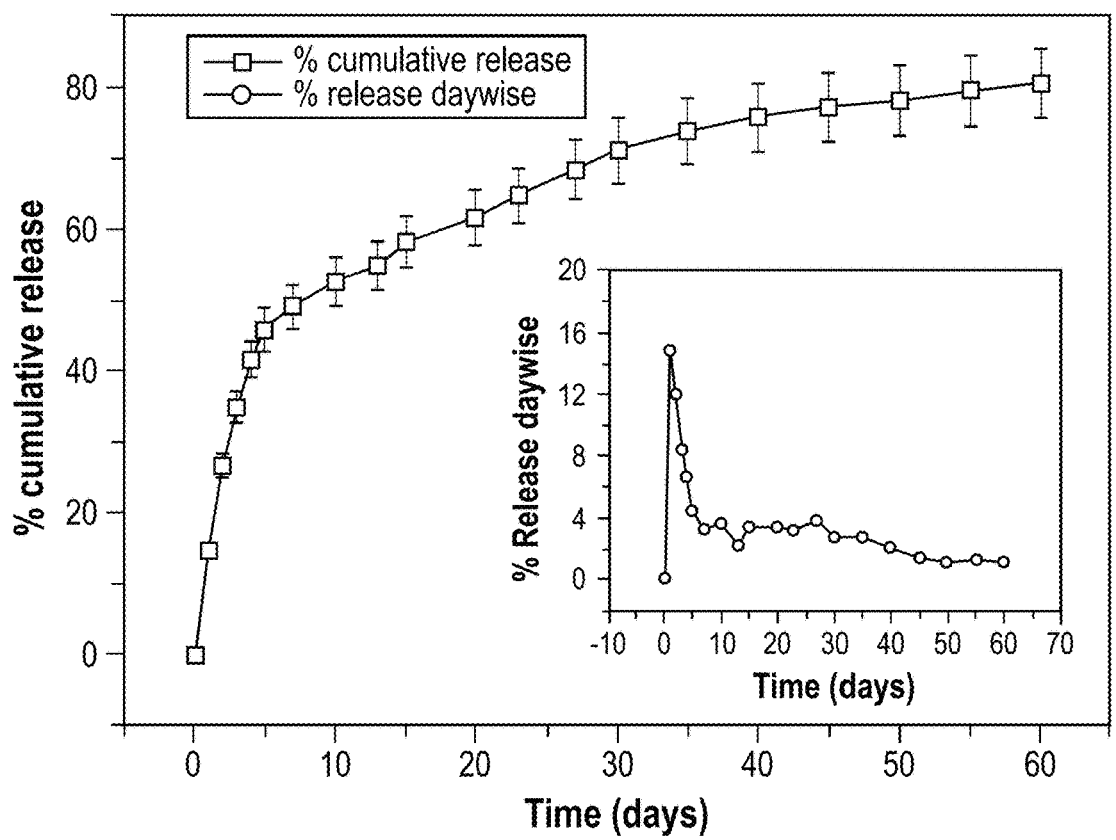
FIG. 14 shows the release data of a MUC1 cytoplasmic domain peptide linked to a polyarginine sequence (RRRRRRRRRCQCRRKN (SEQ ID NO:3)) from PLA-PEG-PPG-PEG nanoparticles.

Evaluation of MUC1 Loaded PLA-PEG-PPG-PEG Nanoparticles:

In-Vitro Release of Encapsulated MUC1 by the Polymeric Nanoparticle PLA-PEG-PPG-PEG A mixture containing 10 ml phosphate buffer saline and 10 mg PLA-PEG-PPG-PEG nanoparticles encapsulating rhodamine B-conjugated to a MUC1 cytoplasmic domain peptide linked to polyarginine protein transduction domain (Ac-RRRRRRRRRCQCRRKN-NH2 (SEQ ID NO:3)) was stirred at 200 rpm at 37° C. Supernatant samples of the mixture were collected by centrifugation at 25,000 rpm at different time intervals for a period of 6 days. The nanoparticles were re-suspended in fresh buffer after each centrifugation. 2 ml of the supernatant was subjected to protein estimation using BCA kit (Pierce, USA) to evaluate the amount of drug release spectrophotometrically at 562 nm. The drug release was calculated by means of a standard calibration curve. It was observed that the release of the drug by the PLA-PEG-PPG-PEG polymeric nanoparticles can be controlled up to 60 days. (FIG. 14).

The XTT (Sodium 2,3,-bis(2-methoxy-4-nitro-5-sulfophenyl)-5-[(phenylamino)-carbonyl]-2H-tetrazolium Inner Salt) Assay Cell viability using XTT (sodium 2,3,-bis(2-methoxy-4-nitro-5-sulfophenyl)-5-[(phenylamino)-carbonyl]-2H-tetrazolium inner salt) assays were carried out in Primary HUVEC cell lines and the MCF-7 cell lines (Table 6).

A total of $1 \times 10^4$ MCF-7 cells were seeded on each well of a 96-well plate and cultured for 24 h. After 24 hours, cells in each plate were treated with polymeric nanoparticles of the present invention containing either 20 or 30 μM of MUC1-cytoplasmic domain peptide linked to a polyarginine sequence (RRRRRRRRRCQCRRKN (SEQ ID NO:3)) or control nanoparticles without any peptide. The cells were incubated with the nanoparticles for different intervals of time ranging from 16 h, 24 h, 48 h, 72 h and 96 h. After incubation, the medium containing PLA-PEG-PPG-PEG nanoparticles loaded with MUC1-cytoplasmic domain peptide was exchanged with fresh medium, and 10 μl of the reconstitute XTT mixture kit reagent were added to each well. After culturing for 4 h, the absorbance of the sample was measured by using a microtiter plate reader (Bio-Rad, CA, U.S.A.) at 450 nm. The proliferation of cells was determined as the percentage of viable cells of the untreated control and analyzed in triplicate. Table 6 shows the effect of MUC1-cytoplasmic domain peptide-loaded PLA-PEG-PPG-PEG nanoparticle on the cell viability of hormone-dependent breast carcinoma cell line, MCF-7.

Those skilled in the art will recognize, or be able to ascertain using no more than routine experimentation, many equivalents to the specific embodiments of the invention described herein. Such equivalents are intended to be encompassed by the following claims.

LIST OF TABLES

Table 1 provides the details of PEG-PPG-PEG block copolymer used for the preparation of the PLA-PEG-PPG-PEG copolymer

| Sl. No. | Mol. wt. | Chemical Name | Composition |
|---|---|---|---|
| 1 | 1100 | PEG-PPG-PEG 1100 | PEG 10% wt. |
| 2 | 4400 | PEG-PPG-PEG 4400 | PEG 30% wt. |
| 3 | 8400 | PEG-PPG-PEG 8400 | PEG 80% wt. |

Table 2 shows the characterization of PLA-PEG-PPG-PEG nanoparticles

| Sample | Particle Size (nm) (Diffraction study) | Zeta ($\zeta$) Potential (surface charge) | PDI (polydispersity index) |
|---|---|---|---|
| PLA | 125 | −15.8 | 0.099 |
| PLA-PEG-PPG-PEG(1100) | 120 | −1.89 | 0.11 |
| PLA-PEG-PPG-PEG (4400) | 117 | −5.86 | 0.105 |
| PLA-PEG-PPG-PEG (8400) | 114 | −3.6 | 0.097 |

Table 3 shows the loading efficacy of the PLA-PEG-PPG-PEG nanoparticles synthesized using varying molecular weights of the polymer PEG-PPG-PEG.

| Nanoparticle | Total Pyrene content (mg/50 mg of PLA) | Loading in NP's (mg/50 mg of PLA) | Percent loading |
|---|---|---|---|
| PLA-PEG-PPG-PEG(1100) | 6.21 | 6.14 | 98.84 |
| PLA-PEG-PPG-PEG(4400) | 2.68 | 2.33 | 96.74 |
| PLA-PEG-PPG-PEG(8400) | 1.74 | 1.69 | 97.29 |

Table 4 provides the loading percent of unmodified anticancer peptide drug, L-PLBCL2P9 in PLA-PEG-PPG-PEG nanoparticles

| Sample | Total Peptide (µg) | Encapsulated peptide (µg) | Loading % |
|---|---|---|---|
| PLA | 2242.49 | 998.27 | 44.52 |
| PLA-PEG-PPG-PEG 1100 | 2242.49 | 1125.34 | 50.18 |
| PLA-PEG-PPG-PEG 4400 | 2242.49 | 1457.99 | 65.02 |
| PLA-PEG-PPG-PEG 8400 | 2242.49 | 1459.77 | 65.10 |

Table 5 provides the loading percent of modified anticancer peptide drug L-PLBCL2P9 in PLA-PEG-PPG-PEG nanoparticles

| Sample | Total Peptide (µg) | Encapsulated peptide (µg) | % Loading |
|---|---|---|---|
| PLA | 2112.23 | 1434.23 | 67.90 |
| PLA-PEG-PPG-PEG 1100 | 2112.23 | 1498.76 | 70.96 |
| PLA-PEG-PPG-PEG 4400 | 2112.23 | 1545.14 | 73.15 |
| PLA-PEG-PPG-PEG 8400 | 2112.23 | 1578.23 | 74.72 |

Table 6 provides the data obtained from proliferation studies of a MUC1 cytoplasmic domain peptide linked to a polyarginine protein transduction domain loaded in PLA-PEG-PPG-PEG nanoparticles. (* indicates a concentration of 1 mg/well)

| Sr. No. | Formulation | Dead Cells | Live Cells | Total Cells | % Dead | Mean (% Dead) | Mean (% Live) |
|---|---|---|---|---|---|---|---|
| 1 | NP'S* | 20000 | 125000 | 145000 | 13.79 | 14.79 | 85.21 |
| 2 |  | 21000 | 112000 | 133000 | 15.79 |  |  |
| 3 | 20 µM | 99500 | 48000 | 147500 | 67.46 | 66.32 | 33.68 |
| 4 | MUC1-NPS | 94500 | 50500 | 145000 | 65.17 |  |  |
| 5 | 30 µM | 97000 | 35500 | 132500 | 73.21 | 72.22 | 27.78 |
| 6 | MUC1-NPS | 99000 | 40000 | 139000 | 71.22 |  |  |
| 7 | PBS | 12500 | 117500 | 130000 | 9.62 | 10.11 | 89.89 |
| 8 | (Control) | 13100 | 110500 | 123600 | 10.60 |  |  |

The invention claimed is:

1. A biodegradable polymeric nanoparticle formed of a block copolymer comprising poly(lactic acid) (PLA) chemically modified with a hydrophilic-hydrophobic block copolymer, wherein said hydrophilic-hydrophobic block copolymer is selected from a block copolymer consisting essentially of poly(methyl methacrylate)-poly(methylacrylic acid) (PMMA-PMAA), poly(styrene-polyacrylic) acid(PS-PAA), poly(acrylic acid)-poly(vinylpyridine) (PAA-PVP), poly(acrylic acid)-poly(N,N-dimethylaminoethyl methacrylate) (PAA-PDMAEMA), poly(ethylene glycol)-poly(butylene glycol) (PEG-PBG), and poly(ethylene glycol)-poly(propylene glycol)-poly(ethylene glycol) (PEG-PPG-PEG).

2. The biodegradable polymeric nanoparticle of claim 1, wherein the biodegradable nanoparticle is formed of the tetra block copolymer PLA-PEG-PPG-PEG.

3. The biodegradable polymeric nanoparticle of claim 1 or 2, wherein the PLA has an average molecular weight in the range of about 4,000 g/mol to 90,000 g/mol.

4. The biodegradable polymeric nanoparticle of claim 2, wherein the PEG-PPG-PEG has an average molecular weight in the range of about 4,000 g/mol to 15,000 g/mol.

5. The biodegradable polymeric nanoparticle of claim 1, wherein the biodegradable nanoparticle is formed of the penta block copolymer PLA-PEG-PPG-PEG-PLA.

6. The biodegradable polymeric nanoparticle of claim 1, wherein the PLA is chemically modified with a hydrophilic-hydrophobic block copolymer using a covalent bond.

7. The biodegradable polymeric nanoparticle of claim 1, wherein the size of the biodegradable polymeric nanoparticle is in the range of about 30 to 120 nm.

8. The biodegradable polymeric nanoparticle of claim 1, wherein the biodegradable polymeric nanoparticle is substantially free of emulsifier.

9. The biodegradable polymeric nanoparticles of claim 1, wherein the biodegradable polymeric nanoparticle further comprises emulsifier at a weight percentage from about 0.5% to 5%.

10. The biodegradable polymeric nanoparticle of claim 1, wherein the average molecular weight of the PLA is in the range of 4,000 to 90,000 g/mol, the average molecular weight of the PEG-PPG-PEG is in the range of about 4,000 g/mol to 15,000 g/mol, and wherein the biodegradable polymeric nanoparticle further comprises emulsifier at a weight percentage from about 0.5% to 5%.

11. The biodegradable polymeric nanoparticle of claim 1, wherein the average molecular weight of the PLA is less than or equal to about 16,000 g/mol, the average molecular weight of the PEG-PPG-PEG is in the range of about 4,000 g/mol to 15,000 g/mol, and wherein the composition is substantially free of emulsifier.

12. The biodegradable polymeric nanoparticle of claim 1 further comprising a therapeutic agent.

13. The biodegradable polymeric nanoparticle of claim 12, wherein the therapeutic agent is encapsulated, surface conjugated, or adsorbed on the biodegradable polymeric nanoparticle.

14. The biodegradable polymeric nanoparticle of claim 13, wherein the therapeutic agent is selected from a group comprising small organic molecules, nucleic acids, polynucleotides, oligonucleotides, nucleosides, DNA, RNA, amino acids, peptides, proteins, antibiotics, low molecular weight molecules, chemotherapeutics, drugs, metal ions, dyes, radioisotopes, contrast agents and imaging agents.

15. The biodegradable polymeric nanoparticle of claim 14, wherein the peptide is an anti-cancer peptide.

16. The biodegradable polymeric nanoparticle of claim 14, wherein the therapeutic agent is a chemotherapeutic.

17. The biodegradable polymeric nanoparticle of claim 16, wherein the chemotherapeutic is selected from the group consisting of paclitaxel, doxorubicin, pimozide, perimethamine, indenoisoquinolines, or nor-indenoisoquinolines.

18. The biodegradable polymeric nanoparticle of claim 1, further comprising a targeting moiety selected from the group consisting of vitamins, small molecule drugs, ligands, amines, peptide fragments, antibodies, and aptamers.

\* \* \* \* \*

SEQUENCE LISTING

<160> NUMBER OF SEQ ID NOS: 5

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Phe Ser Arg Ser Leu His Ser Leu Leu
1               5

```
<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Cys Gln Arg Arg Lys Asn
1               5

<210> SEQ ID NO 3
<211> LENGTH: 16
<212> TYPE: PRT
<213> ORGANISM: Artificial Sequence
<220> FEATURE:
<223> OTHER INFORMATION: Sythetic peptide

<400> SEQUENCE: 3

Arg Arg Arg Arg Arg Arg Arg Arg Arg Cys Gln Cys Arg Arg Lys Asn
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Ala Gln Ala Arg Arg Lys Asn
1               5

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Arg Arg Arg Arg Arg Arg Arg Arg Arg Ala Gln Ala Arg Arg Lys Asn
1               5                   10                  15
```